United States Patent
Chen et al.

(10) Patent No.: US 9,610,257 B2
(45) Date of Patent: Apr. 4, 2017

(54) SMALL MOLECULE XANTHINE OXIDASE INHIBITORS AND METHODS OF USE

(71) Applicant: Baylor College of Medicine, Houston, TX (US)

(72) Inventors: Changyi Chen, Houston, TX (US); Jian-Ming Lu, Pearland, TX (US); Qizhi Yao, Houston, TX (US)

(73) Assignee: BAYLOR COLLEGE OF MEDICINE, Houston, TX (US)

( * ) Notice: Subject to any disclaimer, the term of this patent is extended or adjusted under 35 U.S.C. 154(b) by 161 days.

(21) Appl. No.: 14/483,055

(22) Filed: Sep. 10, 2014

(65) Prior Publication Data

US 2014/0378478 A1 Dec. 25, 2014

Related U.S. Application Data

(63) Continuation of application No. 13/790,083, filed on Mar. 8, 2013, now Pat. No. 8,883,857.

(60) Provisional application No. 61/734,409, filed on Dec. 7, 2012.

(51) Int. Cl.

| A61K 31/11 | (2006.01) |
|---|---|
| C07C 205/44 | (2006.01) |
| A61K 31/185 | (2006.01) |
| A61K 31/277 | (2006.01) |
| A61K 45/06 | (2006.01) |
| C07C 255/56 | (2006.01) |
| C07C 309/44 | (2006.01) |
| C07C 317/22 | (2006.01) |
| A61K 31/519 | (2006.01) |
| C07C 47/544 | (2006.01) |
| C07C 47/565 | (2006.01) |
| C07C 255/57 | (2006.01) |
| C07C 47/54 | (2006.01) |
| C07C 313/04 | (2006.01) |
| A61K 9/00 | (2006.01) |

(52) U.S. Cl.
CPC ............ *A61K 31/11* (2013.01); *A61K 9/0053* (2013.01); *A61K 31/185* (2013.01); *A61K 31/277* (2013.01); *A61K 31/519* (2013.01); *A61K 45/06* (2013.01); *C07C 47/54* (2013.01); *C07C 47/544* (2013.01); *C07C 47/565* (2013.01); *C07C 205/44* (2013.01); *C07C 255/56* (2013.01); *C07C 255/57* (2013.01); *C07C 309/44* (2013.01); *C07C 313/04* (2013.01); *C07C 317/22* (2013.01)

(58) Field of Classification Search
None
See application file for complete search history.

(56) References Cited

U.S. PATENT DOCUMENTS

| 3,931,409 | A | | 1/1976 | Nickel et al. |
|---|---|---|---|---|
| 4,032,522 | A | | 6/1977 | Baldwin et al. |
| 4,087,549 | A | | 5/1978 | Shen et al. |
| 4,125,530 | A | | 11/1978 | Baldwin et al. |
| 4,215,995 | A | | 8/1980 | Turk et al. |
| 4,409,141 | A | | 10/1983 | Noda et al. |
| 4,465,687 | A | | 8/1984 | Doherty et al. |
| 4,694,006 | A | * | 9/1987 | Bundgaard .......... C07D 487/04 514/262.1 |
| 4,977,146 | A | | 12/1990 | Biftu et al. |
| 5,064,837 | A | | 11/1991 | McCombie |
| 5,183,828 | A | | 2/1993 | van't Riet et al. |
| 5,185,363 | A | | 2/1993 | Brooks et al. |
| 5,217,971 | A | | 6/1993 | Takasugi et al. |
| 5,254,338 | A | | 10/1993 | Sakai et al. |
| 5,262,299 | A | | 11/1993 | Evangelista et al. |
| 5,318,971 | A | | 6/1994 | McCombie |
| 5,324,747 | A | | 6/1994 | Carson et al. |
| 5,344,655 | A | | 9/1994 | Sakai et al. |
| 5,356,904 | A | | 10/1994 | Freidinger et al. |
| 5,358,955 | A | | 10/1994 | Brooks et al. |
| 5,426,224 | A | | 6/1995 | Lee et al. |
| 5,428,163 | A | | 6/1995 | Mills |
| 5,446,189 | A | | 8/1995 | Carson et al. |
| 5,455,042 | A | | 10/1995 | Sakai et al. |
| 5,491,132 | A | | 2/1996 | Hemmi et al. |
| 5,493,006 | A | | 2/1996 | De Miranda et al. |
| 5,510,333 | A | | 4/1996 | Angelastro et al. |
| 5,525,711 | A | | 6/1996 | Hawkins et al. |
| 5,543,298 | A | | 8/1996 | Xu et al. |
| 5,563,162 | A | | 10/1996 | Oku et al. |
| 5,565,488 | A | | 10/1996 | Braunlich et al. |
| 5,574,042 | A | | 11/1996 | Oku et al. |
| 5,612,468 | A | | 3/1997 | Hawkins et al. |
| 5,614,520 | A | | 3/1997 | Kondo et al. |
| 5,639,793 | A | | 6/1997 | Lee et al. |
| 5,663,148 | A | | 9/1997 | Or et al. |
| 5,691,351 | A | | 11/1997 | Kolasa et al. |

(Continued)

FOREIGN PATENT DOCUMENTS

| WO | WO-89/09833 | 10/1989 |
|---|---|---|
| WO | WO-90/12008 | 10/1990 |

(Continued)

OTHER PUBLICATIONS

STN document No. 145:383525 referencing JP 2006265174 to Suwa.*
Khallouki et al., Ethnobotanical Survey, Chemical Composition, and Antioxidant Capacity of Methanolic Extract of the Root Bark of Annona cuneata Oliv., Journal of Medicinal Food, vol. 14 Issue 11: Nov. 4, 2011.*
Ford et al., Neonicotinoid Insecticides: Oxidative Stress in Planta and Metallo-oxidase Inhibition, J. Agric. Food Chem., 2011, 59 (9), pp. 4860-4867.*

(Continued)

*Primary Examiner* — Svetlana M Ivanova
(74) *Attorney, Agent, or Firm* — Foley & Lardner LLP

(57) ABSTRACT

Small molecule xanthine oxidase inhibitors are provided, as well as methods for their use in treating gout or hyperuricemia.

7 Claims, 14 Drawing Sheets

(56) References Cited

U.S. PATENT DOCUMENTS

| | | | |
|---|---|---|---|
| 5,691,423 A | 11/1997 | Smith et al. | |
| 5,694,006 A * | 12/1997 | Konopka | H05B 41/28 315/219 |
| 5,698,696 A | 12/1997 | Marciniak et al. | |
| 5,708,173 A | 1/1998 | Oku et al. | |
| 5,714,511 A | 2/1998 | Saavedra et al. | |
| 5,736,548 A | 4/1998 | Bacon et al. | |
| 5,747,499 A | 5/1998 | Bavetsias et al. | |
| 5,750,699 A | 5/1998 | Oku et al. | |
| 5,773,592 A | 6/1998 | Mills | |
| 5,789,417 A | 8/1998 | Boyle et al. | |
| 5,789,447 A | 8/1998 | Wink et al. | |
| 5,792,784 A | 8/1998 | Seguin et al. | |
| 5,910,316 A | 6/1999 | Keefer et al. | |
| 5,922,711 A | 7/1999 | Oku et al. | |
| 5,922,740 A | 7/1999 | Braunlich et al. | |
| 5,929,077 A | 7/1999 | Leftheris | |
| 5,932,737 A | 8/1999 | Itoh et al. | |
| 5,939,460 A | 8/1999 | Ternansky et al. | |
| 5,958,929 A | 9/1999 | Bacon et al. | |
| 5,962,469 A | 10/1999 | Thomas et al. | |
| 5,990,137 A | 11/1999 | Ternansky et al. | |
| 5,994,368 A | 11/1999 | Oku et al. | |
| 6,008,229 A | 12/1999 | Oku et al. | |
| 6,054,303 A | 4/2000 | Davalian et al. | |
| 6,083,959 A | 7/2000 | Oku et al. | |
| 6,083,961 A | 7/2000 | Oku et al. | |
| 6,100,284 A | 8/2000 | Oku et al. | |
| 6,127,356 A | 10/2000 | Crapo et al. | |
| 6,458,829 B1 | 10/2002 | Shen et al. | |
| 6,555,572 B2 | 4/2003 | Lauener et al. | |
| 6,770,658 B2 | 8/2004 | Shen et al. | |
| 7,446,129 B2 | 11/2008 | Lauener et al. | |
| 7,459,479 B2 | 12/2008 | Lauener et al. | |
| 7,842,713 B2 | 11/2010 | Bai et al. | |
| 8,883,857 B2 | 11/2014 | Chen et al. | |
| 8,883,858 B1 | 11/2014 | Chen et al. | |
| 8,895,626 B1 | 11/2014 | Chen et al. | |
| 8,987,337 B2 | 3/2015 | Chen et al. | |
| 2002/0028842 A1 | 3/2002 | Lauener et al. | |
| 2003/0060663 A1 | 3/2003 | Griffin et al. | |
| 2003/0186943 A1 | 10/2003 | Shen et al. | |
| 2003/0220352 A1 | 11/2003 | Lauener et al. | |
| 2004/0023290 A1 | 2/2004 | Griffin et al. | |
| 2007/0208181 A1 | 9/2007 | Lauener et al. | |
| 2008/0113044 A1 | 5/2008 | Alberte et al. | |
| 2008/0275141 A1 | 11/2008 | Whiteford | |
| 2008/0280875 A1 | 11/2008 | Bai et al. | |
| 2010/0016270 A1 | 1/2010 | Whiteford | |
| 2010/0035931 A1 | 2/2010 | Coleman et al. | |
| 2010/0087475 A1 | 4/2010 | Duffield et al. | |
| 2010/0124550 A1 | 5/2010 | Gant et al. | |
| 2010/0197652 A1 | 8/2010 | Bergman et al. | |
| 2010/0226931 A1 | 9/2010 | Valiante et al. | |
| 2010/0310688 A1 | 12/2010 | Chang et al. | |
| 2011/0039821 A1 | 2/2011 | Bai et al. | |
| 2011/0207747 A1 | 8/2011 | Bergman et al. | |
| 2011/0301140 A1 | 12/2011 | Bergman et al. | |
| 2013/0178484 A1 | 7/2013 | Miner et al. | |
| 2014/0163045 A1 | 6/2014 | Chen et al. | |
| 2014/0329909 A1 | 11/2014 | Chen et al. | |
| 2014/0336204 A1 | 11/2014 | Chen et al. | |
| 2014/0336205 A1 | 11/2014 | Chen et al. | |
| 2014/0364508 A1 | 12/2014 | Chen et al. | |
| 2014/0378478 A1 | 12/2014 | Chen et al. | |
| 2014/0378552 A1 | 12/2014 | Chen et al. | |
| 2015/0004699 A1 | 1/2015 | Chen et al. | |
| 2015/0005389 A1 | 1/2015 | Chen et al. | |

FOREIGN PATENT DOCUMENTS

| | | |
|---|---|---|
| WO | WO-92/20357 | 11/1992 |
| WO | WO-94/07518 | 4/1994 |
| WO | WO-94/11354 | 5/1994 |
| WO | WO-95/09158 | 4/1995 |
| WO | WO-95/12394 | 5/1995 |
| WO | WO-96/13485 | 5/1996 |
| WO | WO-96/16981 | 6/1996 |
| WO | WO-96/28437 | 9/1996 |
| WO | WO-96/28448 | 9/1996 |
| WO | WO-96/40223 | 12/1996 |
| WO | WO-97/10218 | 3/1997 |
| WO | WO-97/11069 | 3/1997 |
| WO | WO-97/29090 | 8/1997 |
| WO | WO-97/41104 | 11/1997 |
| WO | WO-98/01120 | 1/1998 |
| WO | WO-98/02440 | 1/1998 |
| WO | WO-98/20001 | 5/1998 |
| WO | WO-98/46590 | 10/1998 |
| WO | WO-99/07351 | 2/1999 |
| WO | WO-99/64037 A1 | 12/1999 |
| WO | WO-00/14083 | 3/2000 |
| WO | WO-00/25787 | 5/2000 |
| WO | WO-00/47057 | 8/2000 |
| WO | WO-00/58308 | 10/2000 |
| WO | WO-2013/159226 | 10/2013 |

OTHER PUBLICATIONS

Xia et al, The Reductive Half-reaction of Xanthine Oxidase, Reaction With Aldehyde Substrates and Identification of the Catalytically Labile Oxygen, Feb. 5, 1999 The Journal of Biological Chemistry 274, 3323-3330.*
Chen et al., Anti-hyperuricemic and nephroprotective effects of Smilax china L, Journal of Ethnopharmacology (2011), 135(2), 399-405.*
STN document No. 142:275871, referencing Panoutsopoulos et al., Kinetics and specificity of guinea pig liver aldehyde oxidase and bovine milk xanthine oxidase towards substituted benzaldehydes, Acta Biochimica Polonica (2004), 51(3), 649-663.*
Pelsy et al., Remarkable positional (regio)specificity of xanthine oxidase and some dehydrogenases in the reactions with substituted benzaldehydes, as evidenced by STN document No. 98:103343.*
Baldwin et al., 4-Trifluoromethylimidazoles and 5-(4-pyridyl)-1,2,4-triazoles, new classes of xanthine oxidase inhibitors, Journal of Medicinal Chemistry (1975), 18(9), 895-900.*
Hyun et al., Photo-protection by 3-bromo-4,5-dihydroxybenzaldehyde against ultraviolet B-induced oxidative stress in human keratinocytes, Ecotoxicology and Environmental Safety, vol. 83, Sep. 1, 2012, pp. 71-78.*
U.S. Appl. No. 14/681,020, filed Apr. 7, 2015.
Beiler et al.The Inhibition of Xanthine Oxidase by Flavonoids and Related Compounds. J Biol Chem. Oct. 1951, vol. 192(2), pp. 831-834. [Downloaded from www.jbc.org] p. 831, para 4 to p. 832, para 3; p. 833, Table 1.
Aversa et al., "The inhibition of xanthine oxidase by acetaldehyde in aqueous solution," Physiol Chem Phys Med NMR, (1996), 28:153-162.
Batthyany et al., "Reversible post-translational modification of proteins by nitrated fatty acids in vivo," J Biol Chem, (2006), 281:20450-20463.
Borgulya et al., "Catechol-0-methyltransferase-Inhibiting Pyrocatechol Derivatives: Synthesis and Structure-Activity Studies," Helvetica Chimica Acta, (1989), 72:952-968.
Carroll et al., "A simplified alkaline phosphotungstate assay for uric acid in serum," Clin Chem., (1971), 17:158-160.
Dhalla et al., "Role of oxidative stress in cardiovascular diseases," J. Hypertens, (2000), 18:655-673.
Eggebean, A.T., "Gout: An Update," Am Fam Physician, (2007), 76:801-808.
Enroth et al., "Crystal structures of bovine milk xanthine dehydrogenase and xanthine oxidase: structure-based mechanism of conversion," Proc Natl Acad Sci USA, (2000), 97:10723-10728.
Higgins et al., "The potential for xanthine oxidase inhibition in the prevention and treatment of cardiovascular and cerebrovascular disease," Cardiovasc Psychiatry Neurol., (2009), Article ID 282059, 9 pages.
Johnson et al., "Allantoxanamide: a potent new uricase inhibitor in vivo," Life Sci., (1978), 23:2239-2244.

(56) References Cited

OTHER PUBLICATIONS

Kelley et al., "Nitro-oleic acid, a novel and irreversible inhibitor of xanthine oxidoreductase," J Biol Chem., (2008), 283: 36176-36184.
Lu, J., et al., "Dihydroxy Nitrobenzaldehyde (DHNB) is a Potent Xanthine Oxidase Inhibitor," Abstract, Academic Surgical Congress, published in Journal of Surgical Research,(2012), 172(2):350.
Medina-Campos et al., "S-allylcysteine scavenges singlet oxygen and hypochlorous acid and protects LLC-PK(1) cells of potassium dichromate-induced toxicity," Food Chem Toxicol, (2007), 45:2030-2039.
Metz et al., "A combined QM/MM study on the reductive half-reaction of xanthine oxidase: substrate orientation and mechanism," J Am Chem Soc., (2009), 131:14885-14902.
Morpeth et al., "Inhibition of Xanthine Oxidase by Various Aldehydes," Biochemistry, (1984), 23:1332-1338.
Okamoto et al., "An extremely potent inhibitor of xanthine oxidoreductase. Crystal structure of the enzyme-inhibitor complex and mechanism of inhibition," J Biol Chem., (2003), 278:1848-1855.
Pauff et al., "Inhibition studies of bovine xanthine oxidase by luteolin, silibinin, quercetin, and curcumin," J Nat Prod., (2009), 72:725-731.
Perez et al., "Dihydroxynitrobenzaldehydes and hydroxymethoxynitrobenzaldehydes: synthesis and biological activity as catechol-0-methyltransferase inhibitors," J Med Chem., (1992), 35:4584-4588.
PubChem Compound ID: 100733; 3,4-dihydroxybenzyl alcohol; 4 pages. Mar. 26, 2005.
PubChem Compound ID: 104091; 3,5-dinitro-4-hydroxybenzaldehyde; 5 pages. Mar. 27, 2005.
PubChem Compound ID: 11961166; AKOS006293497; 4 pages. Dec. 11, 2006.
PubChem Compound ID: 12173; terephthalaldehyde; 4 pages. Mar. 26, 2005.
PubChem Compound ID: 13401256; 5-nitroisophthalaldehyde; 5 pages. Feb. 8, 2007.
PubChem Compound ID: 1712303; 3,5-dinitrobenzaldehyde; 4 pages. Jul. 12, 2005.
PubChem Compound ID: 18169; 4-hydroxy-3-nitrobenzaldehyde; 5 pages. Mar. 26, 2005.
PubChem Compound ID: 34777; isophthalaldehyde; 4 pages. Mar. 26, 2005.
PubChem Compound ID: 3782344; 4,5-dihydroxy-2-nitrobenzaldehyde; 6 pages. Jul. 19, 2005.
PubChem Compound ID: 4807; o-phthalaldehyde; 5 pages. Mar. 25, 2005.
PubChem Compound ID: 5748957; 3,4-Dihydroxy-5-nitrobenzaldehyde; 4 pages. Aug. 9, 2005.
PubChem Compound ID: 69712; 3-hydroxy-4-nitrobenzaldehyde; 4 pages. Mar. 28, 2005.
PubChem Compound ID: 7449; 3-nitrobenzaldehyde; 4 pages. Mar. 26, 2005.
PubChem Compound ID: 75571; 3,5-dinitrosalicyladehyde; 4 pages. Mar. 27, 2005.
PubChem Compound ID: 818107; 4-hydroxy-5-nitrobenzene-1,3-dicarbaldehyde; 3 pages. Jul. 9, 2005.
PubChem Compound ID: 83651; 3,4,5-trihydroxybenzaldehyde; 4 pages. Mar. 26, 2005.
PubChem Compound ID: 8768; protocatechualdehyde; 6 pages. Mar. 26, 2005.
Sato et al., "Design, synthesis, and pharmacological and pharmacokinetic evaluation of 3-phenyl-5-pyridyl-1,2,4-triazole derivatives as xanthine oxidoreductase inhibitors," Bioorg Med Chem Lett., (2009), 19:184-187.
Sato et al., "Discovery of 3-(2-cyano-4-pyridyl)-5-(4-pyridyl)-1,2,4-triazole, FYX-051—a xanthine oxidoreductase inhibitor for the treatment of hyperuricemia [corrected]," Bioorg Med Chem Lett., (2009), 19:6225-6229.
Schroder et al., "Xanthine oxidase inhibitor tungsten prevents the development of atherosclerosis in ApoE knockout mice fed a Western-type diet," Free Radie Biol Med., (2006), 41:1353-1360.
Weakley et al., "Natural antioxidant dihydroxybenzyl alcohol blocks ritonavir-induced endothelial dysfunction in porcine pulmonary arteries and human endothelial cells," Med Sci Monit., (2011), 17:BR235-241.
Wikberg et al., "Identification of Major Metabolites of the Catechol-0-Methyltransferase Inhibitor Entacapone in Rats and Humans," Drug Metabolism and Disposition, (1993), 21(1):81-92.
Yonetani et al., "Decreasing effect of allantoxanamide, a hyperuricemic agent on renal functions in rats," Jpn J Pharmacol., (1987), 45:37-43.
Yu et al., "The dual actions of morin (3,5,7,2',4'-pentahydroxyflavone) as a hypouricemic agent: uricosuric effect and xanthine oxidase inhibitory activity," J Pharmacol Exp Ther., (2006), 316:169-175.
Zhao et al., "Antioxidative effect of melatonin on DNA and erythrocytes against free-radical-induced oxidation," Chem Phys Lipids., (2008) 151:77-84.
Baldwin et al. 4-Trifluoromethylimidazoles and 5-(4-pyridyl)-1,2,4-triazoles, new classes of xanthine oxidase inhibitors, Journal of Medicinal Chemistry 1975, 18 9, 895-900.
Bommarius et al., Xanthine Oxidase Reactivity in Reversed Micellar Systems: A Contribution to the Prediction of Enzymic Activity in Organized Media, Journal of the American Chemical Society (1995), 117(16), 4515-23.
Farid Khallouki, Ethnobotanical Survey, Chemical Composition, and Antioxidant Capacity of Methanolic Extract of the Root Bark of Annona Cuneata Oliv. Journal of Medicinal Food, vol. 14 Issue 11: Nov. 4, 2011.
Ford et al., Neonicotnoid Insecticides: Oxidative Stress in Planta and Metallo-oxidase Inhibition, J Argic. Food Chem., 2011, 59(9), pp. 4860-4867.
Hyun, et al., Photo-protection by 3-bromo-4, 5-dihydroxybenzaldehyde against ultraviolet B-induced oxidative stress in human keratinocytes, Ecotoxicology and Environmental Safety, vol. 83, Sep. 1, 2012, pp. 71-78.
Panoutsopoulos, Kinetics and Specificity of Guinea Pig Live Aldehyde Oxidase and Bovine Milk Xanthine Oxidase Towards Substiuted Benzaldehydes, Acta Biochimica Polonica, (2004), 51(3), 649-663.
Pelsy et al., Remarkable Positional Regio Specificity of Xanthine Oxidase and some Dehydrogenase in the Reactions with Substituted Benzaldehydes, as Evidence by STN document No. 98: 103343; Accession No. 1983:103343 (1983).
Revised Ford et al., Neonicotnoid Insecticides: Oxidative Stress in Planta and Metallo-oxidase Inhibition, J Argic. Food Chem., 2011, 59(9), pp. 4860-4867.
Xia et al, The Reductive Half-Reaction of Xanthine Oxidase, Reaction with Aldehyde Substrates and Identification of the Catalytically Liable Oxygen, Feb. 5, 1999, The Journal of Biological Chemistry 274, 3323-3330.
Chen et al., "Anti-hyperuricemic and nephroprotective effects of Similax china L," Journal of Ethnopharmacology, (2011), 135(2):399-405.
STN Document No. 118:38915, 1991.
STN Document No. 141:106248, 2004.
STN Document No. 144:184031, 2006.
STN document No. 145:383525 referencing JP 2006265174 to Suwa, 2006.
STN Document No. 146:107412, 2009.
STN Document No. 146:434574, 2008.
Wang et al. ("Wang"), Natural Products Research: Formerly Natural Product Letters 21:3, 196-202, 2007.

* cited by examiner

SMALL MOLECULE XANTHINE OXIDASE INHIBITORS AND METHODS OF USE

CROSS-REFERENCE TO RELATED APPLICATIONS

This application is a continuing application and claims priority to U.S. patent application Ser. No. 13/790,083 filed on Mar. 8, 2013 entitled "Small Molecule Xanthine Oxidase Inhibitors And Methods Of Use" which claims the benefit of and incorporates by reference U.S. provisional patent Application No. 61/734,409, filed on Dec. 7, 2012 and entitled "Small Molecule Xanthine Oxidase Inhibitors And Methods Of Use."Each application is hereby incorporated by reference in its entirety for all of its teachings.

BACKGROUND

Gout is caused by hyperuricemia, namely, abnormally high levels of uric acid in the blood. Gout is usually present as acute inflammatory arthritis, as well as tophi, kidney stones, or urate nephropathy. Gout affects 1-2% of adults in developed countries and represents the most common case of inflammatory arthritis in men. In the United States, gouty arthritis accounts for millions of outpatient visits annually. Furthermore, gout and hyperuricemia are associated with chronic diseases such as hypertension, diabetes mellitus, metabolic syndrome, and renal and cardiovascular disease.

Xanthine oxidase (XO) is a form of a molybdoflavin protein, xanthine oxidoreductase (XOR). It plays an important role in the catabolism of purines in humans, as it catalyzes the oxidation of hypoxanthine to xanthine and then catalyzes the oxidation of xanthine to uric acid. Meanwhile, reactive oxygen species (ROS), including superoxide and $H_2O_2$, are generated during this process. Uric acid can serve as an antioxidant to prevent macromolecular damage by ROS. However, overproduction of uric acid can cause hyperuricemia and lead to gout and other diseases. Therefore, maintaining uric acid at normal levels represents an important therapeutic goal for the prevention of gout and related disorders. For most patients with primary gout, overproduction of uric acid is the primary cause of hyperuricemia.

Currently, two drugs have been developed to treat gout. Allopurinol is the most commonly used therapy for chronic gout and has been used clinically for more than 40 years. Allopurinol lowers uric acid production by inhibiting XO activity, and is used as a first-line urate-lowering phamacotherapy. Allopurinol, a structural isomer of hypoxanthine, is hydroxylated by XO to oxypurinol, which coordinates tightly to the reduced form of the molybdenum center, replacing the Mo—OH group of the native enzyme. Unfortunately, while rare, allopurinol has life-threatening side effects such as a hypersensitivity syndrome consisting of fever, skin rash, eosinophilia, hepatitis, and renal toxicity, for which the mortality rate approaches 20%. It also causes Stevens-Johnson syndrome (SJS) and toxic epidermal necrolysis (TENS), two life-threatening dermatological conditions. Febuxostat, a non-purine xanthine oxidase inhibitor, has been approved for the management of gout in Europe and the United States. Side effects associated with febuxostat therapy include elevated serum liver enzymes, nausea, diarrhea, arthralgia, headache, and rash. The drugs available for treatment and prevention of hyperuricemia and gout remain limited. Therefore, safe and effective xanthine oxidase inhibitors are needed.

SUMMARY

Provided herein are small molecule xanthine oxidase inhibitors. Also provided herein are methods for their use in treating gout or hyperuricemia. A class of xanthine oxidase inhibitors described herein includes compounds of the following structure:

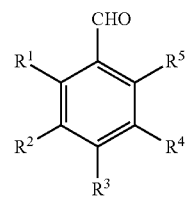

and pharmaceutically acceptable salts thereof. In these compounds, $R^1$, $R^2$, $R^3$, $R^4$, and $R^5$ are each independently selected from hydrogen, hydroxyl, nitro, cyano, fluoro, chloro, bromo, trifluoromethyl, sulfonyl, and aldehyde, wherein $R^1$, $R^2$, $R^3$, $R^4$, and $R^5$ are not simultaneously hydrogen. Examples of suitable xanthine oxidase inhibitors as described herein include the following compounds:

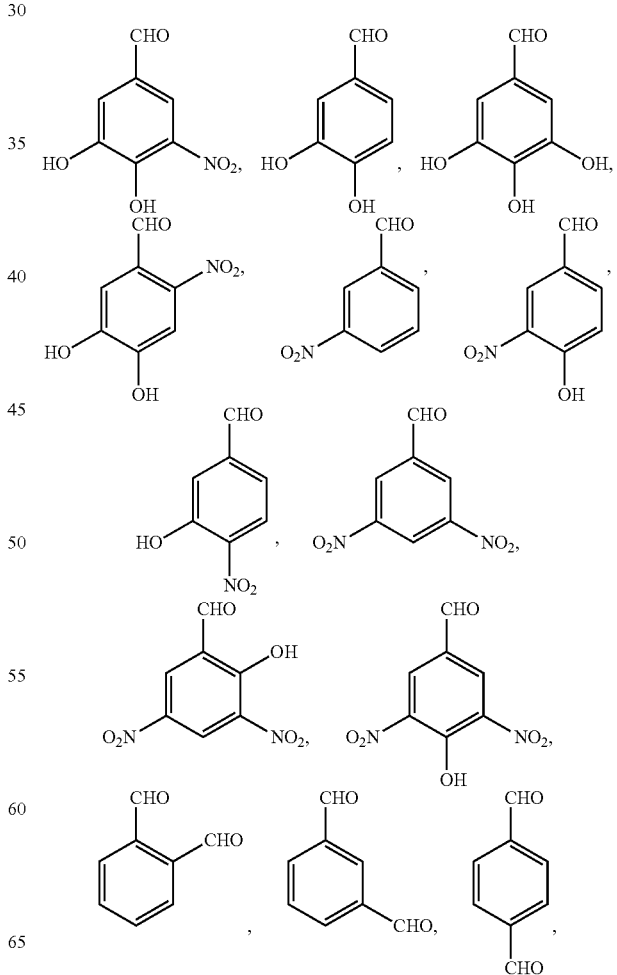

-continued

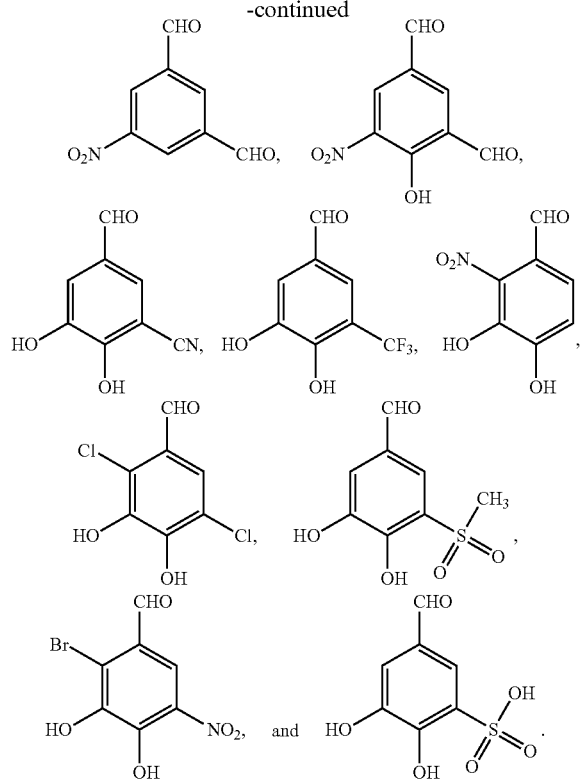

A xanthine oxidase inhibitor suitable for the methods described herein also includes the following compound:

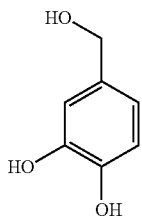

and pharmaceutically acceptable salts thereof.

Also provided herein are methods for treating gout or hyperuricemia in a subject. A method of treating gout or hyperuricemia in a subject includes administering to the subject an effective amount of a xanthine oxidase inhibitor as described herein. Optionally, the methods for treating gout or hyperuricemia in a subject can further include administering a second therapeutic agent, such as an anti-gout agent (e.g., allopurinol, benzbromarone, colchicine, probenecid, or sulfinpyrazone), an anti-inflammatory agent, or an antioxidant, to the subject. Optionally, the compound is administered orally to the subject.

Further provided herein are methods for reducing uric acid production and/or reactive oxygen species production in a subject. The methods include administering to the subject an effective amount of a xanthine oxidase inhibitor as described herein. Optionally, the methods for reducing uric acid production and/or reactive oxygen species production further comprise selecting a subject having gout or hyperuricemia.

Methods of inhibiting xanthine oxidase activity in a cell are also provided herein. The methods include contacting a cell with an effective amount of a xanthine oxidase inhibitor as described herein. Optionally, the contacting is performed in vivo. Optionally, the contacting is performed in vitro.

The details of one or more embodiments are set forth in the drawings and the description below. Other features, objects, and advantages will be apparent from the description and drawings, and from the claims.

DETAILED DESCRIPTION

Figure 1A:
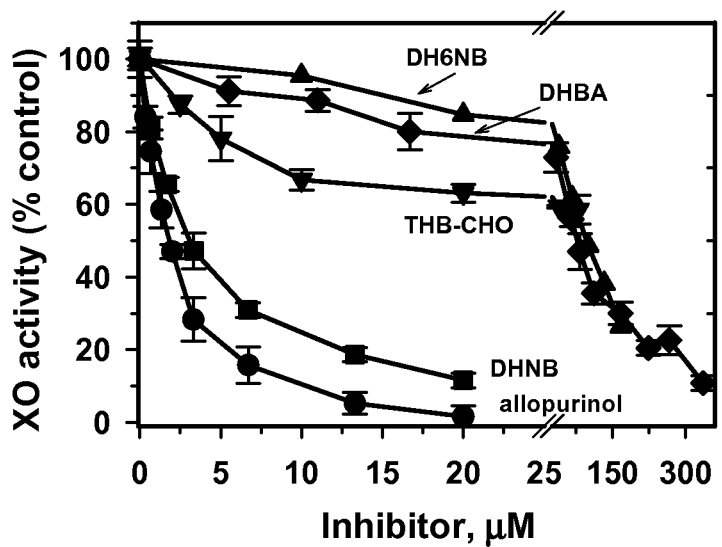
FIG. 1A is a graph showing the inhibition of xanthine oxidase (XO) activity by test compounds (DH6NB, DHBA, THB-CHO, and DHNB) and a control compound (allopurinol).

Provided herein are small molecule xanthine oxidase inhibitors and methods for their use in treating gout or hyperuricemia in a subject. The xanthine oxidase inhibitors are administered in an effective amount to treat gout or hyperuricemia in a subject.

I. Compounds

A class of xanthine oxidase inhibitors described herein is represented by Formula I:

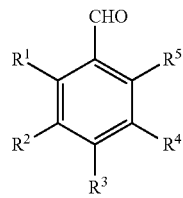

and pharmaceutically acceptable salts thereof.

In Formula I, $R^1$, $R^2$, $R^3$, $R^4$, and $R^5$ are each independently selected from hydrogen, hydroxyl, nitro, cyano, fluoro, chloro, bromo, trifluoromethyl, sulfonyl, and aldehyde (i.e., —CHO). Optionally, the sulfonyl is methylsulfonyl or sulfonic acid.

Also, in Formula I, $R^1$, $R^2$, $R^3$, $R^4$, and $R^5$ are not simultaneously hydrogen.

Examples of Formula I include the following compounds:

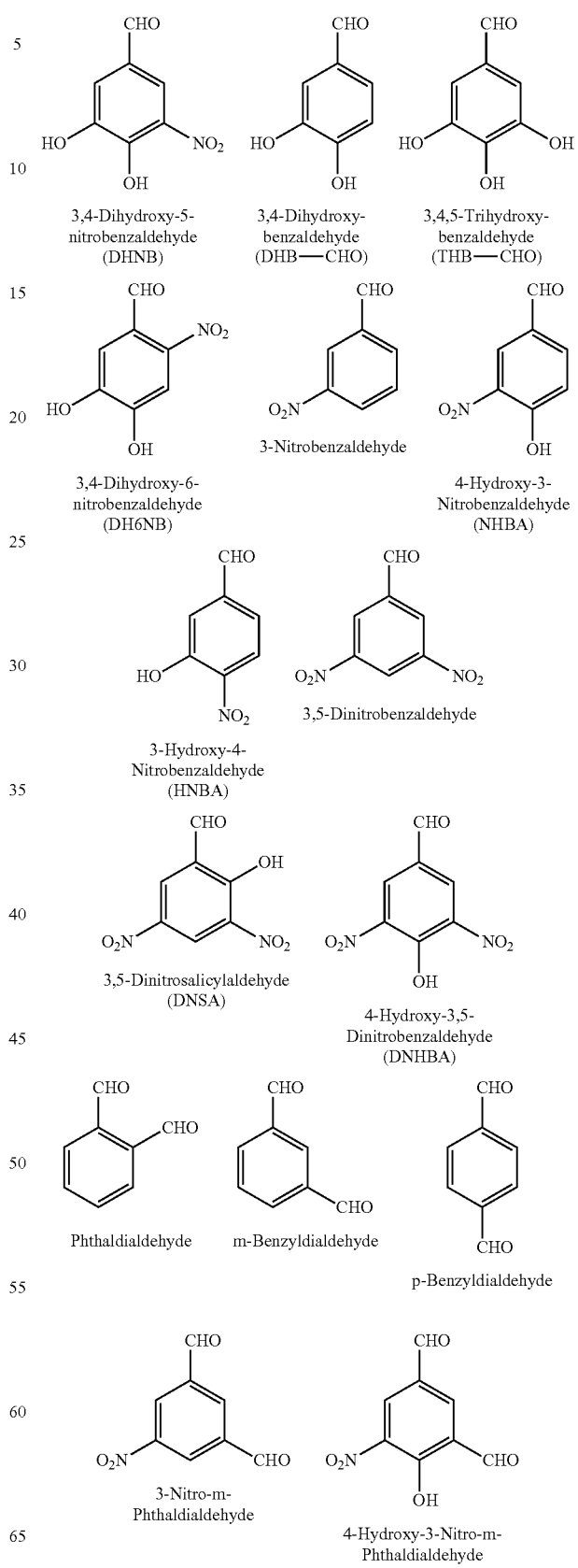

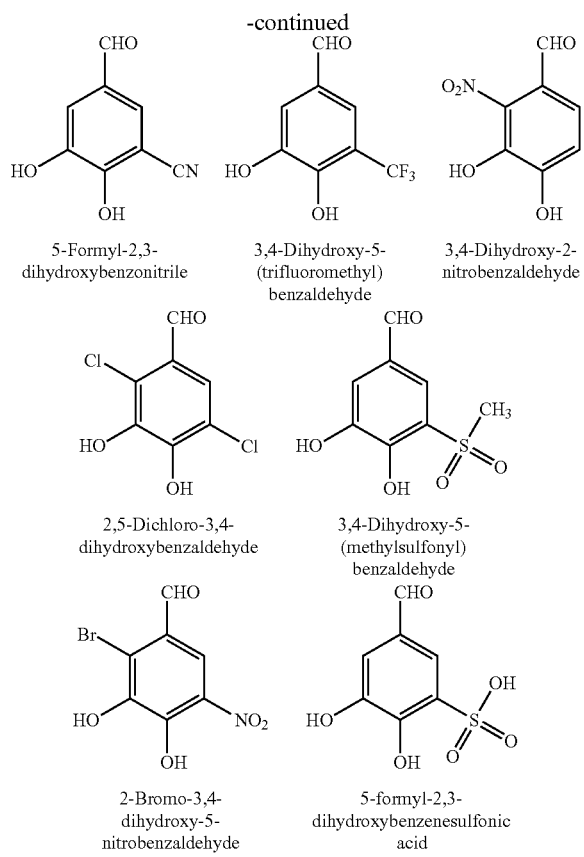

5-Formyl-2,3-dihydroxybenzonitrile 3,4-Dihydroxy-5-(trifluoromethyl)benzaldehyde 3,4-Dihydroxy-2-nitrobenzaldehyde 2,5-Dichloro-3,4-dihydroxybenzaldehyde 3,4-Dihydroxy-5-(methylsulfonyl)benzaldehyde 2-Bromo-3,4-dihydroxy-5-nitrobenzaldehyde 5-formyl-2,3-dihydroxybenzenesulfonic acid An additional xanthine oxidase inhibitor useful with the methods described herein includes the following compound:

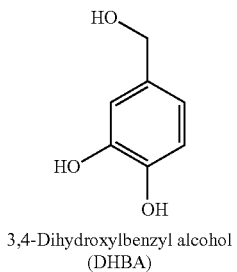

3,4-Dihydroxylbenzyl alcohol (DHBA)

and pharmaceutically acceptable salts thereof.

II. Pharmaceutical Formulations

The compounds described herein or derivatives thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the compound described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers, such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers, such as polyvinylpyrrolidone; amino acids such as glycine, glutamine, asparagine, arginine or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN® (ICI, Inc.; Bridgewater, N.J.), polyethylene glycol (PEG), and PLURONICS™ (BASF; Florham Park, N.J.).

Compositions containing the compounds described herein or derivatives thereof suitable for parenteral injection may comprise physiologically acceptable sterile aqueous or non-aqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants, such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier), such as sodium citrate or dicalcium phosphate, or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, may contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or derivatives thereof for rectal administrations are optionally suppositories, which can be prepared by mixing the compounds with suitable non-irritating excipients or carriers, such as cocoa butter, polyethyleneglycol or a suppository wax, which are solid at ordinary temperatures but liquid at body temperature and, therefore, melt in the rectum or vaginal cavity and release the active component.

Dosage forms for topical administration of the compounds described herein or derivatives thereof include ointments, powders, sprays, and inhalants. The compounds described herein or derivatives thereof are admixed under sterile conditions with a physiologically acceptable carrier and any preservatives, buffers, or propellants as may be required. Ophthalmic formulations, ointments, powders, and solutions are also contemplated as being within the scope of the compositions.

The compositions can include one or more of the compounds described herein and a pharmaceutically acceptable carrier. As used herein, the term pharmaceutically acceptable salt refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Barge et al., *J. Pharm. Sci.* (1977) 66, 1, which is incorporated herein by reference in its entirety, at least, for compositions taught therein.) Administration of the compounds and compositions described herein or pharmaceutically acceptable salts thereof can be carried out using therapeutically effective amounts of the compounds and compositions described herein or pharmaceutically acceptable salts thereof as described herein for periods of time effective to treat a disorder. The effective amount of the compounds and compositions described herein or pharmaceutically acceptable salts thereof as described herein may be determined by one of ordinary skill in the art and includes exemplary dosage amounts for a mammal of from about 0.5 to about 200 mg/kg of body weight of active compound per day, which may be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. Those of skill in the art will understand that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

III. Methods of Making the Compounds

The compounds described herein can be prepared in a variety of ways known to one skilled in the art of organic synthesis or variations thereon as appreciated by those skilled in the art. The compounds described herein can be prepared from readily available starting materials. Optimum reaction conditions may vary with the particular reactants or solvents used, but such conditions can be determined by one skilled in the art.

Variations on Formula I and the compounds described herein include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high performance liquid chromatography (HPLC) or thin layer chromatography.

Optionally, the compounds described herein can be obtained from commercial sources. The compounds can be obtained from, for example, Sigma Chemical Co. (St. Louis, Mo.), VWR International (Radnor, Pa.), or Oakwood Products, Inc. (West Columbia, S.C.).

IV. Methods of Use

Provided herein are methods of treating or preventing gout and hyperuricemia in a subject. The methods include administering to a subject an effective amount of one or more of the compounds or compositions described herein, or a pharmaceutically acceptable salt thereof. The expression "effective amount," when used to describe an amount of compound in a method, refers to the amount of a compound that achieves the desired pharmacological effect or other effect, for example, an amount that results in uric acid production reduction. The compounds and compositions described herein or pharmaceutically acceptable salts thereof are useful for treating gout or hyperuricemia in humans, including, without limitation, pediatric and geriatric populations, and in animals, e.g., veterinary applications. Optionally, the methods are used to treat conditions associated with elevated uric acid levels, including chronic gouty arthritis, acute inflammatory arthritis, uric acid nephropathy, kidney stones, or tophi.

Further described herein are methods of reducing uric acid production and/or reactive oxygen species production in a subject. The methods include administering to the subject one or more of the compounds as described herein. Optionally, the methods can further comprise selecting a subject having gout or hyperuricemia.

The methods described herein can further comprise administering to the subject a second therapeutic agent. Thus, the provided compositions and methods can include one or more additional agents. The one or more additional agents and the compounds described herein or pharmaceutically acceptable salts thereof can be administered in any order, including concomitant, simultaneous, or sequential administration. Sequential administration can be temporally spaced order of up to several days apart. The methods can also include more than a single administration of the one or more additional agents and/or the compounds described herein or pharmaceutically acceptable salts or prodrugs thereof. The administration of the one or more additional agents and the compounds described herein or pharmaceutically acceptable salts or prodrugs thereof can be by the same or different routes and concurrently or sequentially.

Therapeutic agents include, but are not limited to, anti-gout agents. For example, the anti-gout agent can be allopurinol, benzbromarone, colchicine, probenecid, or sulfinpyrazone. Therapeutic agents also include anti-inflammatory agents. Examples of suitable anti-inflammatory agents include, for example, steroidal and nonsteroidal anti-inflammatory drugs (e.g., ibuprofen and prednisone). The therapeutic agent can also be, for example, an antioxidant. Examples of suitable antioxidants include, for example, α-tocopherol, beta-carotene, butylated hydroxyanisole (BHA), butylated hydroxytoluene (BHT), caffeic acid, lutein, lycopene, selenium, tert-butylhydroquinone (TBHQ), Vitamin A, Vitamin C, and Vitamin E. Further examples of suitable antioxidants include putative antioxidant botanticals, such as, for example, grape seeds, green tea, *Scutellaria baicalensis*, American ginseng, ginkgo biloba, and the like.

Any of the aforementioned therapeutic agents can be used in any combination with the compositions described herein. Combinations are administered either concomitantly (e.g., as an admixture), separately but simultaneously (e.g., via separate intravenous lines into the same subject), or sequentially (e.g., one of the compounds or agents is given first followed by the second). Thus, the term combination is used to refer to concomitant, simultaneous, or sequential administration of two or more agents.

The methods and compounds as described herein are useful for both prophylactic and therapeutic treatment. For prophylactic use, a therapeutically effective amount of the compounds and compositions or pharmaceutically acceptable salts thereof as described herein are administered to a subject prior to onset (e.g., before obvious signs of gout or hyperuricemia), during early onset (e.g., upon initial signs and symptoms of gout or hyperuricemia), or after the development of gout or hyperuricemia. Prophylactic administration can occur for several days to years prior to the manifestation of symptoms of gout or hyperuricemia. Therapeutic treatment involves administering to a subject a therapeutically effective amount of the compounds and compositions or pharmaceutically acceptable salts thereof as described herein after gout or hyperuricemia is diagnosed.

The methods and compounds described herein are also useful in inhibiting xanthine oxidase activity in a cell. The methods include contacting a cell with an effective amount of a xanthine oxidase inhibitor as described herein. Optionally, the contacting is performed in vivo. Optionally, the contacting is performed in vitro.

V. Kits

Also provided herein are kits for treating or preventing gout or hyperuricemia in a subject. A kit can include any of the compounds or compositions described herein. For example, a kit can include a compound of Formula I or any of the compounds described herein. A kit can further include one or more additional agents, such as anti-gout agents (e.g., allopurinol, benzbromarone, colchicine, probenecid, or sulfinpyrazone), anti-inflammatory agents, or antioxidants. A kit can include an oral formulation of any of the compounds or compositions described herein. A kit can additionally include directions for use of the kit (e.g., instructions for treating a subject), a container, a means for administering the compounds or compositions, and/or a carrier.

As used herein the terms treatment, treat, or treating refer to a method of reducing one or more symptoms of a disease or condition. Thus in the disclosed method, treatment can refer to a 10%, 20%, 30%, 40%, 50%, 60%, 70%, 80%, 90%, or 100% reduction in the severity of one or more symptoms of the disease or condition. For example, a method for treating a disease is considered to be a treatment if there is a 10% reduction in one or more symptoms or signs of the disease in a subject as compared to a control. As used herein, control refers to the untreated condition. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refer to an action, for example, administration of a composition or therapeutic agent, that occurs before or at about the same time a subject begins to show one or more symptoms of the disease or disorder, which inhibits or delays onset or severity of one or more symptoms of the disease or disorder.

As used herein, references to decreasing, reducing, or inhibiting include a change of 10%, 20%, 30%, 40%, 50%, 60%, 70%, 80%, 90% or greater as compared to a control level. Such terms can include, but do not necessarily include, complete elimination.

As used herein, subject means both mammals and non-mammals. Mammals include, for example, humans; non-human primates, e.g., apes and monkeys; cattle; horses; sheep; rats; mice; pigs; and goats. Non-mammals include, for example, fish and birds.

Throughout this application, various publications are referenced. The disclosures of these publications in their entireties are hereby incorporated by reference into this application.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the subject matter described herein which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Xanthine oxidase from bovine milk, xanthine, allopurinol, 3,4-dihydroxybenzaldehyde, phosphate buffered saline (PBS) solution, potassium nitrite ($KNO_2$), dioxide manganese ($MnO_2$), diethylene-triamine-pentaacetic acid (DTPA), EDTA, ferrous ammonium sulfate, hydrogen peroxide ($H_2O_2$), sodium hypochlorite, DPPH, 5,5'-dithio-bis(2-nitrobenzoic acid) (DTNB), sodium borohydride, potassium persulfate, ascorbic acid, and (±)-α-tocopherol were obtained from Sigma Chemical Co. (St. Louis, Mo.). 3,4-Dihydroxy-5-nitrobenzaldehyde, 3,4-dimethoxybenzyl alcohol, 3,4-dihydroxyphenyl ethanol, caffeic acid, 3,4-dihydroxyphenyl ethanol, 3,4,5-trihydroxybenzaldehyde hydrate, 4-hydroxy-3-methoxybenzyl alcohol, and 3,4-dihydroxybenzoic acid were obtained from VWR International (Radnor, Pa.). 3,4-Dihydroxy-6-nitrobenzaldehyde was obtained from Oakwood Products, Inc. (West Columbia, S.C.).

Data are presented as mean±SD as compared to the negative control. Statistical significance was determined by a Student's t-test (two tailed). A value of P<0.05 was considered significant.

Example 1

XO Inhibition Assay

XO activity was determined by the method of continuous spectrophotometric rate determination by monitoring the increase of absorption at 295 nm of uric acid in 67 mM phosphate buffer (pH 7.4) containing 20 nM xanthine oxidase with an activity of 5 mU/ml, with or without the compounds as described herein. After pre-incubation for 1 to 5 min at 25° C., the formation of uric acid in the reaction mixture was initiated by the addition of 50 μM xanthine. The test compounds and positive control are shown in Scheme 1. Allopurinol was used as a positive control. All compounds, including allopurinol, were dissolved in $H_2O$ or an aqueous solution. $H_2O$ was used as the negative control.

Scheme 1:

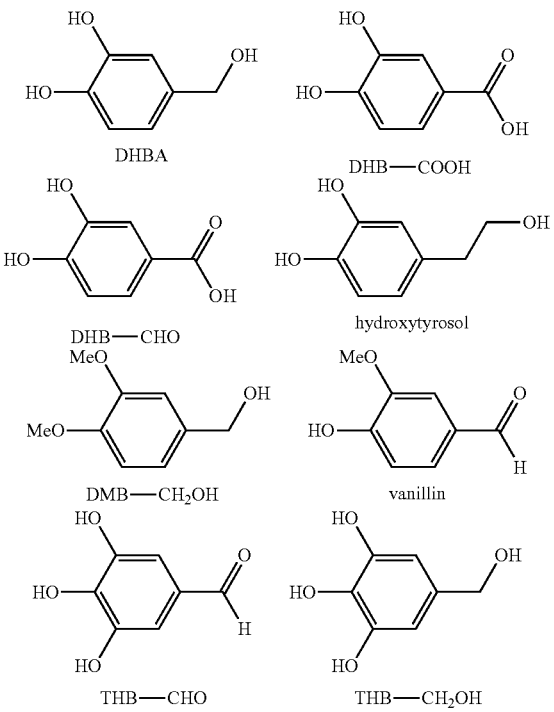

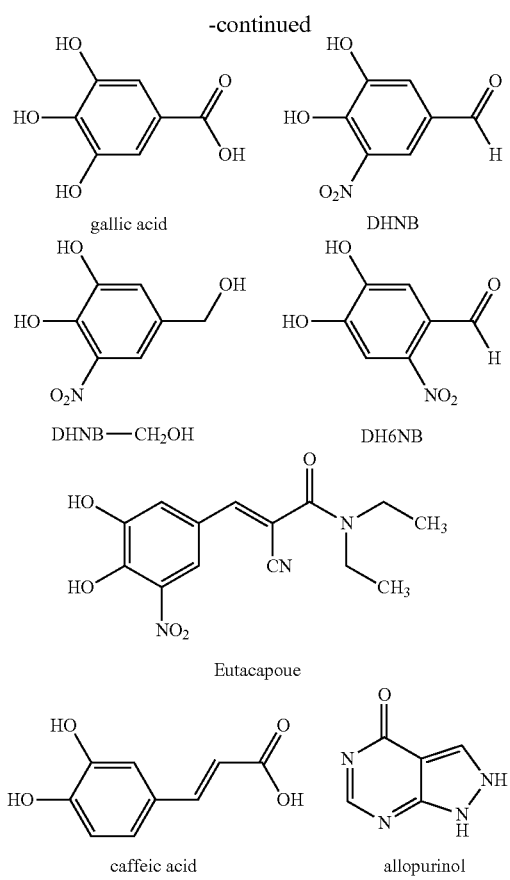

Figure 1B:
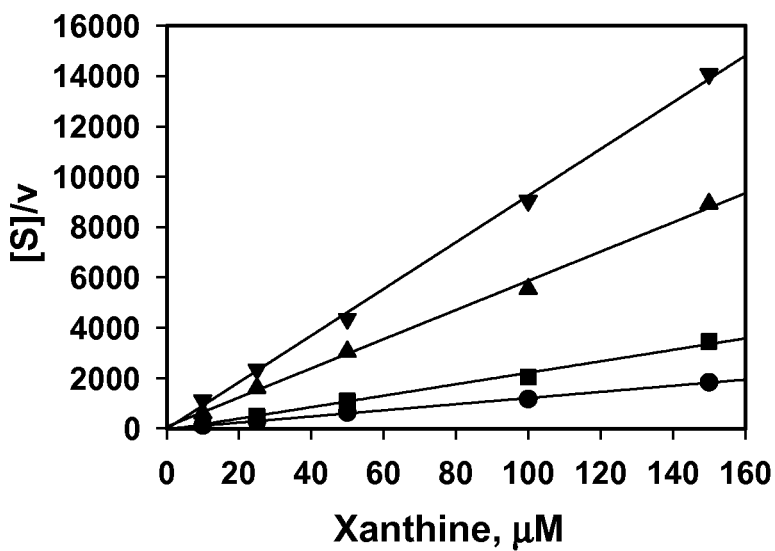
FIG. 1B is a Dixon Plot for DHNB at varying concentrations of xanthine.
Figure 1C:
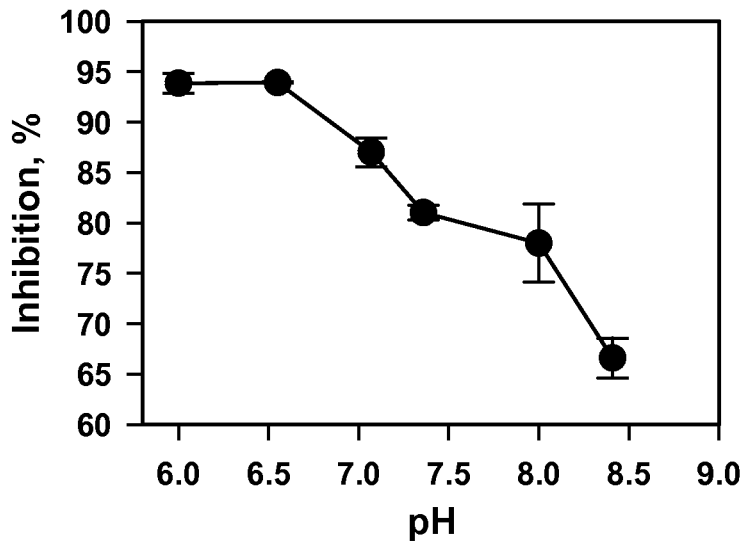
FIG. 1C is a graph showing the effects of pH on the inhibitory effect of DHNB on XO.

XO inhibition—The inhibitory activity of xanthine oxidase by DHNB, DHBA, DH6NB and THB-CHO was determined in vitro by the formation of uric acid, which was measured spectrophotometrically by following the increase in absorbance of uric acid at 295 nm. When 20 nM XO was mixed with increasing concentrations of allopurinol, DHNB, DH6NB, DHBA, or THB-CHO (Scheme 1), the initial rate of uric acid formation showed a concentration-dependent decrease compared to the control, reflecting the decrease of XO activity (see FIG. 1A). DHNB significantly inhibited XO activity with an $IC_{50}$ value of 3 µM, which is close to allopurinol's value of 1.8 µM. The $IC_{50}$ values for DHBA and DH6NB were 76 and 96 µM, respectively, indicating weak inhibition of XO activity. The $IC_{50}$ value for THB-CHO was too high to determine. After DHNB and XO were pre-incubated for 1 min, xanthine was added to initiate the reaction. The initial rate of uric acid formation did not change with increasing concentrations of xanthine. A Dixon plot of a steady-state kinetic study of DHNB inhibition on XO activity indicated that the initial rates did not change with increasing xanthine concentrations when the concentration of DHNB was fixed (see FIG. 1B). The pH dependence of DHNB inhibition indicated that neutral or slightly acidic solutions benefit the inhibition (see FIG. 1C).

Figure 2:
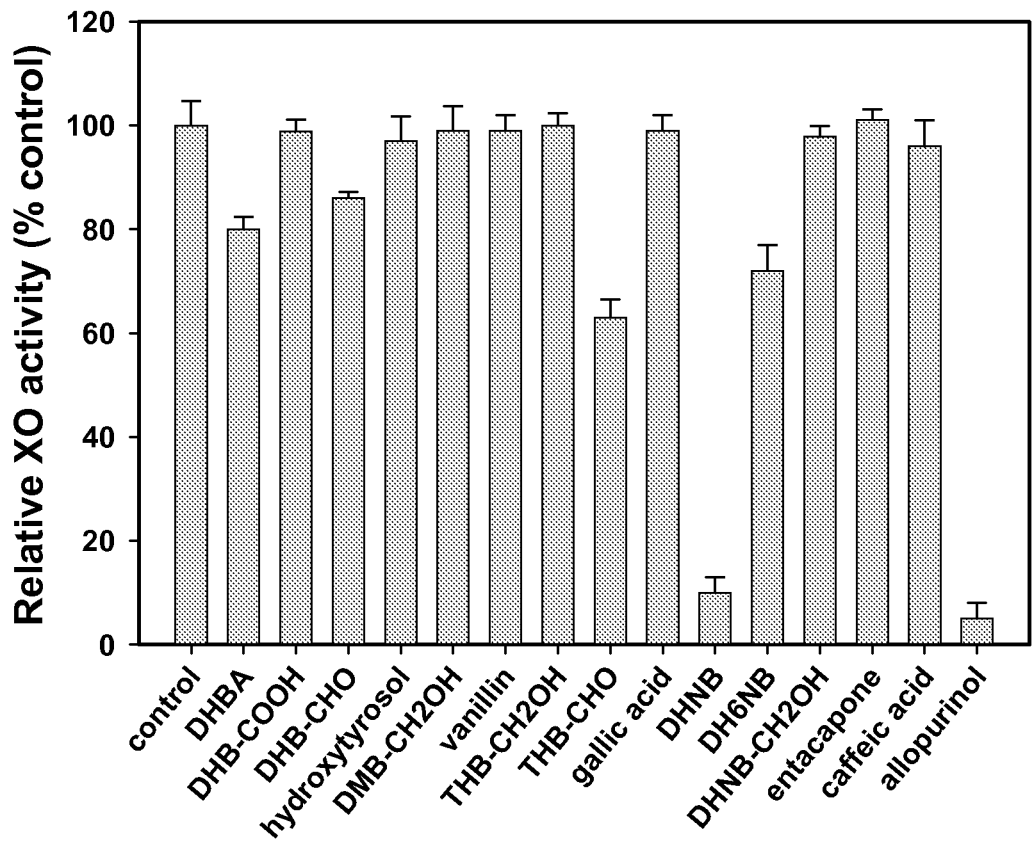
FIG. 2 is a graph comparing the xanthine oxidase inhibitory effects of catechol compounds, each at a concentration of 20 μM. The control represents no inhibitor added.

Structure activity relationship of XO inhibition—The inhibition of XO activity by the other compounds shown in Scheme 1, including a drug entacapone, was also studied. These compounds possess the same catechol skeleton in their structures but with different functional groups. The ability of each compound to inhibit XO at a concentration of 20 µM was compared with that of allopurinol (see FIG. 2). Although these compounds have similar structures, their XO inhibition capacities were different. Compounds containing a —CHO group, such as DHNB, DH6NB, DHB-CHO and THB-CHO, had inhibitory effects on XO. Vanillin, although containing a —CHO group, had no inhibition on XO activity. DHBA has no —CHO group but it showed moderate inhibition. Other compounds, such as DHB-COOH, gallic acid, caffeic acid, hydroxytyrosol, DMB-$CH_2OH$ and DHNB-$CH_2OH$, containing —COOH or —$CH_2OH$, had no effect on XO.

Entacapone, the catechol-O-methyl transferase (COMT) inhibitor, did not show any inhibitory effect on XO even though it possesses a 3,4-dihydroxy-5-nitrobenzyl moiety, as does DHNB, the strong XO inhibitor.

Figure 3:
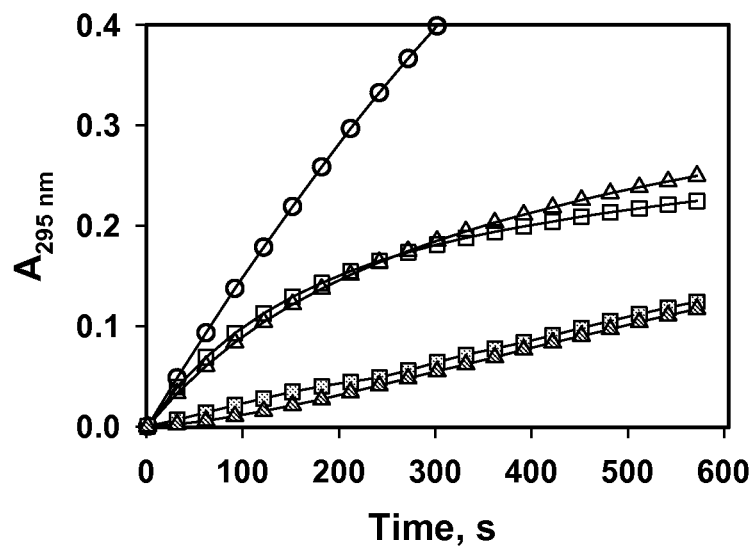
FIG. 3 is a graph showing the time course of inhibition of xanthine oxidase activity by DHNB and allopurinol. XO activity was determined under standard conditions and started by adding 20 nM XO (open symbols) or by adding 50 μM xanthine following 4 min pre-incubation of XO and inhibitor (solid symbols). Circles, control—no inhibitor added; squares, with 6.67 μM allopurinol; triangle, with 6.67 μM DHNB.
Figure 4:
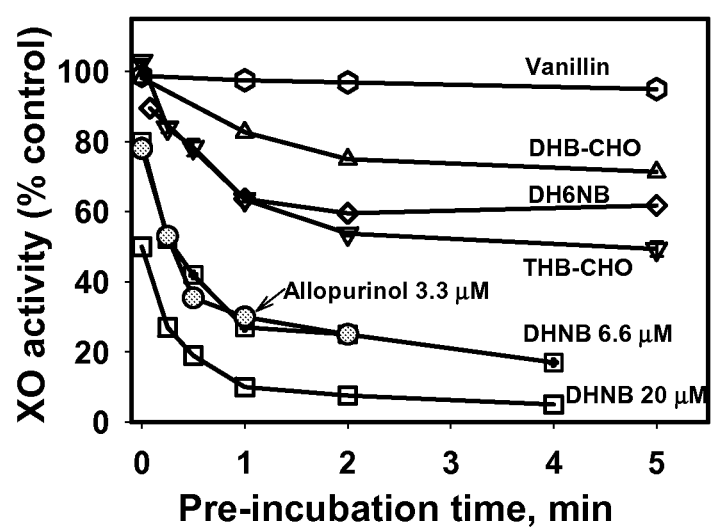
FIG. 4 is a graph showing the influence of pre-incubation of 20 μM inhibitors with 20 nM XO on XO activity. Vanillin, DHB-CHO, DH6NB, THB-CHO, allopurinol (at 3.3 μM), and DHNB (at 6.6 μM and 20 μM) were the tested compounds.
Figure 5:
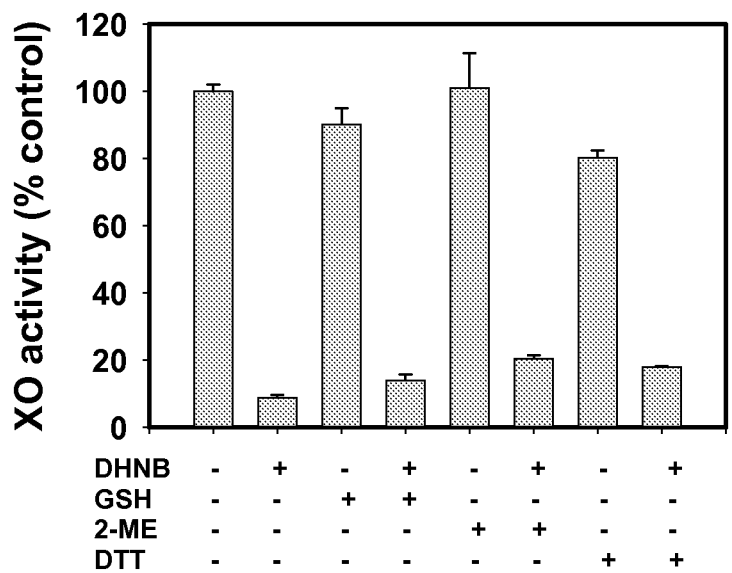
FIG. 5 is a graph demonstrating that DHNB inhibition of XO is not reversible by reducing agents. XO (10 mU/ml) and 20 μM DHNB were pre-incubated for 10 min at 25° C. in phosphate buffer (100 mM pH 7.4). Then a high level of GSH (20 mM), 2-mercaptoethanol (2-ME, 20 mM), or dithiothreitol (DTT, 20 mM) was added for 15 min, and XO activity was analyzed by the production of uric acid. A "+" signifies the addition of the reagent DHNB, GSH, 2-ME, and/or DTT. A "−" signifies that the reagent was not added. Data represent the mean±S.E. at least three independent determinations.

XO inhibition of DHNB is irreversible—DHNB displayed time-dependent inhibition of XO activity, similar to that of allopurinol. When XO (20 nM) was added to the mixture of xanthine (50 µM) and the inhibitor (6.67 µM) to start the reaction, both DHNB and allopurinol showed time-dependent inhibition (see FIG. 3). An excess of 6.67 µM DHNB or 6.67 µM allopurinol reduced the rate gradually and finally reached a steady state level of catalytic activity. No complete inactivation was observed at the tested condition. After pre-incubation of 20 nM XO with 10 µM DHNB or 10 µM allopurinol for 4 min, the catalytic activity of XO displayed a steady state from the beginning and both DHNB and allopurinol showed a similar inhibitory pattern. Furthermore, after pre-incubation of the DHNB and XO for 0 to 5 min at 25° C., the formation of uric acid in the reaction mixture was initiated by the addition of 50 µM xanthine. Pre-incubation of the DHNB and XO significantly increased the inhibition. For example, 6.67 µM DHNB only inhibited 20% of XO activity without pre-incubation, as determined by comparing with the control of the initial rate in the first 200 s. However, after a 2-min incubation of DHNB and XO, the inhibition was increased to 75%. Meanwhile, pre-incubation also affected the XO inhibition of DH6NB, DHB-CHO, and THB-CHO (see FIG. 4). The inhibition of DHB-CHO on XO activity was not concentration dependent but instead was pre-incubation time dependent. However, pre-incubation of XO and DHBA did not increase the inhibition potency of DHBA. For other compounds listed in Scheme 1, such as vanillin, DHB-COOH, hydroxytyrosol, DMB-$CH_2OH$, THB-$CH_2OH$, gallic acid, DHNB-$CH_2OH$, caffeic acid, and entacapone, pre-incubation with XO for up to 5 min did not show any inhibitory effect. These results indicate that DHNB is an irreversible XO inhibitor in the tested condition. Also, XO was treated with 20 µM DHNB to induce inhibition; the reaction mixture was then treated with high levels of glutathione (GSH; 20 mM), dithiothreitol (DTT; 20 mM) or 2-mercaptoethanol (2-ME; 20 mM), which did not abolish the inhibition (see FIG. 5).

Example 2

Conversion of DHNB to Products by XO

The reaction kinetics of DHNB with XO at different pH values were measured using a spectrophotometer by monitoring the decay of DHNB at 327 nm in a system of 30 nM XO with 30 µM DHNB in phosphate buffer with pH 6.5 to 8.5. The extinction coefficient of DHNB at 327 nm was measured as 15,600 $M^{-1}$ $cm^{-1}$. The sample for product analysis by mass spectroscopy and HPLC was prepared by mixing 0.3 U XO with 4 mg DHNB in 1 mL phosphate buffer (pH 7.4) for 3 days. The DHNB/XO samples were analyzed by HPLC (Bio-Rad BioLogic DuoFlow; Hercules, Calif.) equipped with a 250×4.6 mm, 5 micron Phenomenex C-18 (2) Luna column, with a mobile phase of 40% acetonitrile/water. DHNB and its product were monitored by the optical absorption at 279 nm and 327 nm.

Negative electrospray ionization-mass spectrometry (ESI-MS) and tandem (MS-MS) were applied to detect and confirm the reaction products of DHNB with XO. All mass spectrometric experiments were performed on an API 3200-Qtrap triple quadrupole mass spectrometer (Applied Biosystem/MDS SCIEX; Foster City, Calif.) equipped with a turbolonSpray™ source. The main working parameters for mass spectrum were set as follows: ion-spray voltage, −4.5 kV; ion source temperature, 600° C.; gas 1, 40 psi; gas 2, 40 psi; curtain gas, 20 psi; collision gas, high.

Figure 6A:
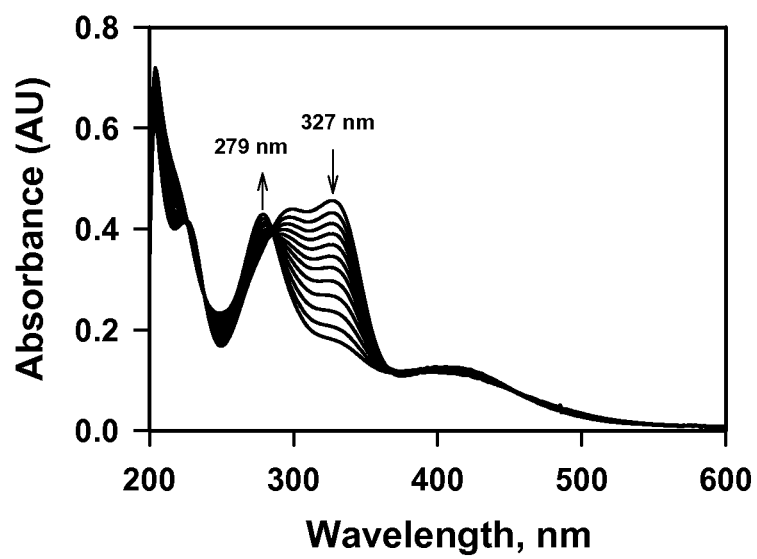
FIG. 6A is a graph of the time course of absorption change of DHNB (327 nm, arrow indicates decrease) and the formation of the product (279 nm, arrow indicates increase) following the mixing of 30 nM XO and 30 μM DHNB in 0.1M phosphate buffer (pH 7.4).
Figure 6B:
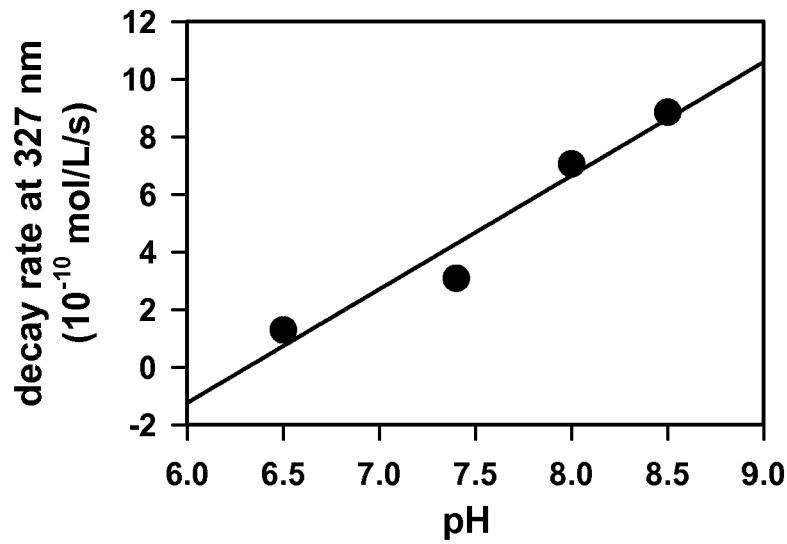
FIG. 6B is a graph showing the effects of pH on the conversion of DHNB by XO enzyme.
Figure 6C:
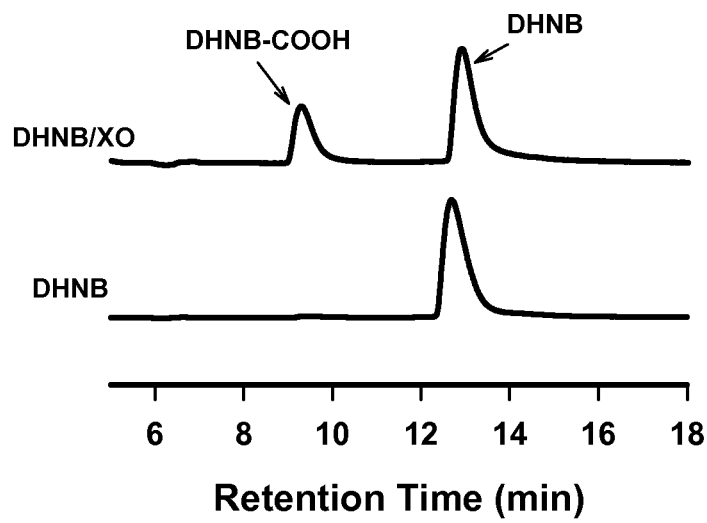
FIG. 6C contains an HPLC profile of DHNB (control) and a DHNB/XO mixture after incubation for 3 days.
Figure 6D:
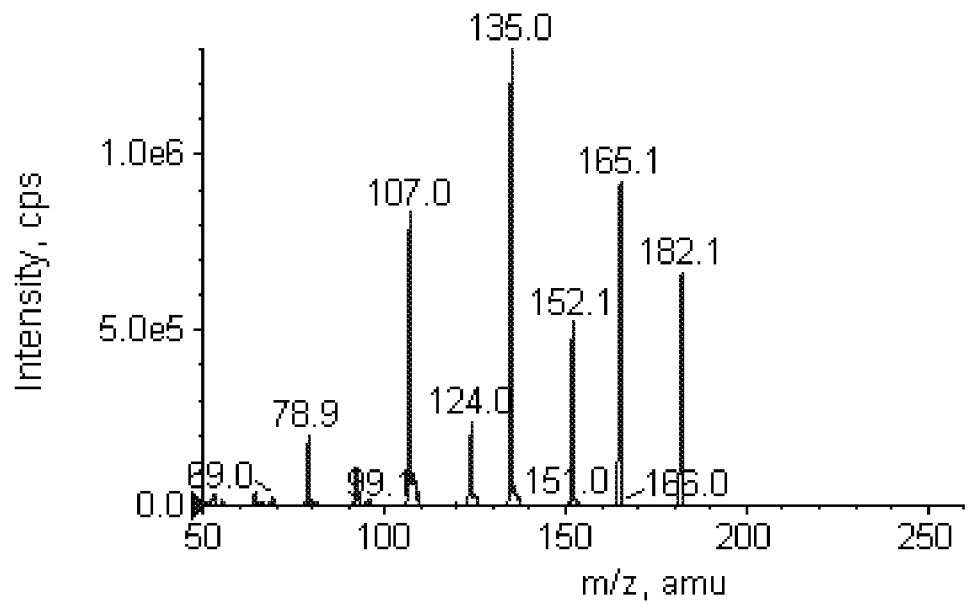
FIG. 6D is a MS/MS spectrum of DHNB.
Figure 6E:
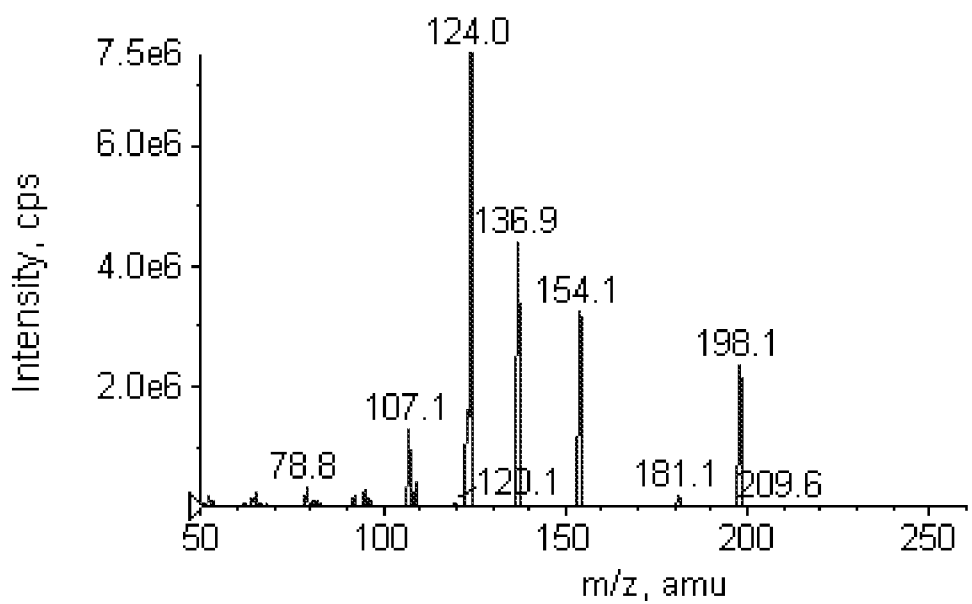
FIG. 6E is a MS/MS spectrum of the DHNB/XO product, DHNB-COOH.

Reaction of XO and DHNB—To determine how DHNB inhibits XO enzyme activity, 30 μM DHNB was incubated with 15 mU/ml (or 30 nM) XO in phosphate buffer (pH 7.4) and xanthine was then added to initiate the reaction as discussed above. The inhibition of DHNB on XO activity lasted up to 20 h. After that, the enzymatic activity of XO was recovered. The optical spectral change of DHNB was measured in a system without xanthine, i.e., 30 μM DHNB with 15 mU/ml (or 30 nM) XO in phosphate buffer. The absorption of DHNB at 327 nm decreased with time and a new peak appeared at 270 nm (see FIG. 6A). The decay rate was in the range of $10^{-10}$ mol/L/s and was pH dependent, i.e., the higher the pH value, the faster DHNB decayed (see FIG. 6B). Without XO, however, DHNB itself was very stable. At room temperature, DHNB was converted by XO enzyme to a product which has no inhibitory effect on XO and thus recovered the XO activity as the concentration of DHNB decreased. The UV-VIS spectrum of the product was different from that of DHNB. HPLC analysis of DHNB/XO showed a new peak which was more polar than DHNB (see FIG. 6C). Mass spectrometric analysis of the product gave a molecular ion ([M-H]$^-$) peak at m/z 198 in the EI mass spectrum, while DHNB showed [M-H]$^-$ peak at m/z 182 (see FIGS. 6D, E). The MS/MS of m/z 182 of DHNB gave several typical fragments such as m/z 165 ([M-H—OH]$^-$), 152 ([M-H—CHO—H]$^-$) and 135 (m/z 152-OH). However, the MS/MS of molecular ion at m/z 198 of the product gave a first main fragment at m/z 154, a mass difference of 44 indicating a loss of $CO_2$, which further loses a —OH to give a fragment at m/z 137. Based on the mass spectrum, the product is 3,4-dihydroxy-5-nitrobenzoic acid, implying that DHNB is oxidized to the acid by the enzyme.

Example 3

Antioxidant Activity of DHNB

In addition, unlike allopurinol, the compounds described herein can serve as antioxidants. This was determined by testing the ability of the compounds to scavenge DPPH, HOCl, peroxynitrite, and the superoxide ion. Each experiment was performed three times and the data are presented as mean±SD.

DPPH scavenging assay—The abilities of the polyphenols described herein to scavenge the DPPH radical were measured optically by monitoring the decreases of their absorptions at 429 nm. The DPPH scavenging activities of DHNB, DH6NB, DHBA, DHB-CHO, THB-CHO, and allopurinol were assayed at a concentration of 20 μM (FIG. 7A). DPPH was used at a concentration of 100 μM. Their scavenging activities were compared with that of vitamin C. As shown in FIG. 7A, DHNB, DH6NB, DHBA, DHB-CHO, and THB-CHO have as strong of a DPPH scavenging effect as vitamin C; however, allopurinol has no scavenging effect on DPPH. The concentration dependent effects of compounds DHNB, DHBA, DHB-CHO, and allopurinol on DPPH scavenging activity were also studied and compared with that of vitamins C and E (FIG. 8).

HOCl scavenging assay —HOCl was prepared immediately before use by adjusting the pH of a 1% (v/v) solution of NaOCl to pH 6.2 with 0.6 M sulfuric acid. The concentration was further determined spectrophotometrically at 235 nm using the molar extinction coefficient of 100 $M^{-1}$ $cm^{-1}$. 5-Thio-2-nitrobenzoic acid (TNB) was prepared by reducing 5,5'-dithio-bis(2-nitrobenzoic acid) (DTNB) with sodium borohydride in phosphate buffer. The final concentrations of reagents used in the assay are as follows: 25 μM HOCl, 70 μM TNB, 0 to 200 μM antioxidants, phosphate buffer, 50 mM, pH 6.6. The HOCl scavenging assay was based on the inhibition of TNB oxidation to DTNB induced by HOCl.

Figure 9:
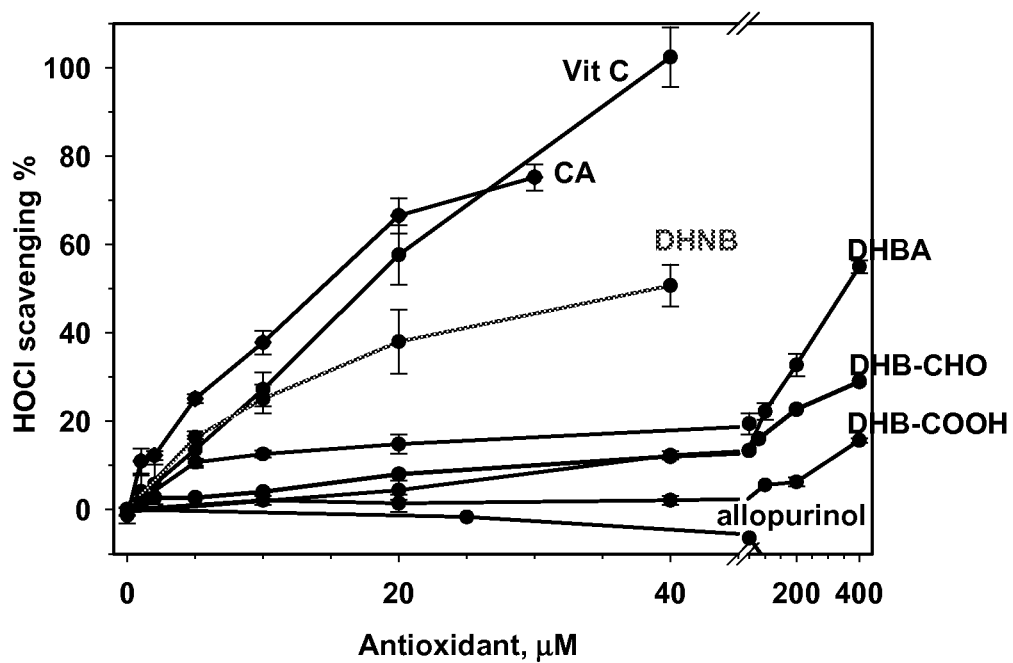
FIG. 9 is a graph showing the concentration dependent HOCl scavenging activities of DHNB, caffeic acid (CA), DHBA, DHB-CHO, DHB-COOH, and allopurinol. Vitamin C (Vit C) was used as a control.

At 20 μM, THB-CHO had a stronger HOCl scavenging effect than that of vitamin C. DHNB had a moderate scavenging effect, while other compounds, including DHBA, DHB-CHO, and DH6NB, had a weak scavenging effect on HOCl (FIG. 7B). The concentration dependent effect of these compounds, including DHNB, caffeic acid, DHBA, DHB-CHO, DHB-COOH, and allopurinol, on HOCl scavenging activity were also studied and compared with that of Vitamin C (FIG. 9).

Peroxynitrite scavenging assay—Peroxynitrite (ONOO$^-$) was generated by mixing 5 mL acidic solution (0.6 M HCl) of $H_2O_2$ (0.7 M) and 5 mL of 0.6 M $KNO_2$ in an ice bath for 1 second and the reaction was quenched with 5 mL of ice-cold 1.2 M NaOH. Residual $H_2O_2$ was removed using granular $MnO_2$ prewashed with 1.2 M NaOH and the reaction mixture was then left overnight at −20° C. Concentrations of ONOO$^-$ were determined before each experiment at 302 nm using a molar extinction coefficient of 1,670 $M^{-1}$ $cm^{-1}$. The final concentrations of reagents used in the assay are as follows: 25 μM ONOO$^-$, 10 μM DTPA, 5 μM DHR 123, 0.1 M phosphate buffer, pH 7.4. The ONOO$^-$ scavenging assay was performed by monitoring the oxidation of dihydrorhodamine (DHR 123) by ONOO$^-$ spectrophotometrically at 500 nm.

Figure 10:
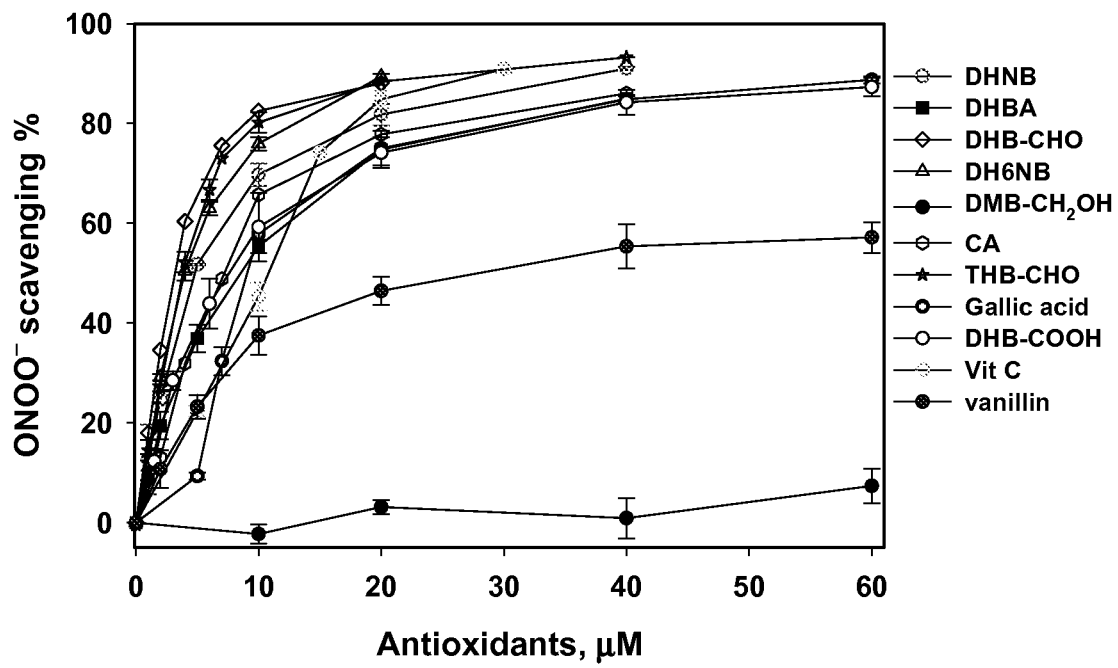
FIG. 10 is a graph showing the concentration dependent peroxynitrite scavenging activity of DHNB, DHBA, DHB-CHO, DH6NB, DMB-CH$_2$OH, caffeic acid, THB-CHO, gallic acid, DHB-COOH, and vanillin. Vitamin C (Vit C) was used as a control.

The abilities of DHNB, DHBA, DHB-CHO, DH6NB, caffeic acid, THB-CHO, gallic acid, vanillin, and DMB-$CH_2OH$ to scavenge peroxynitrite were compared with that of vitamin C. DHNB, DHBA, DHB-CHO, DH6NB, caffeic acid, THB-CHO and gallic acid had a strong scavenging effect on ONOO$^-$ (FIG. 7C). Vitamin C was used as a positive control. The concentration dependent effects of these compounds on ONOO$^-$ scavenging were also studied and compared with that of vitamins C and E (FIG. 10).

Superoxide scavenging assay—Superoxide ($O_2^-$.) scavenging activity was assayed in the xanthine-xanthine oxidase system and determined by the inhibition of the reduction of nitro blue tetrazolium (NBT) to form blue formazan which has an absorption at 560 nm. The final concentrations of reagents used in the assay are as follows: 16.8 mU xanthine oxidase, 25 μM xanthine, 50 μM NBT, and 0.1M phosphate buffer (pH 8.5). $O_2^-$. production and xanthine oxidase activity were measured as NBT reduction (at 560 nm) and uric acid production (at 295 nm), respectively. The abilities of polyphenols to scavenge $O_2^-$. were compared with that of GSH.

Figure 11:
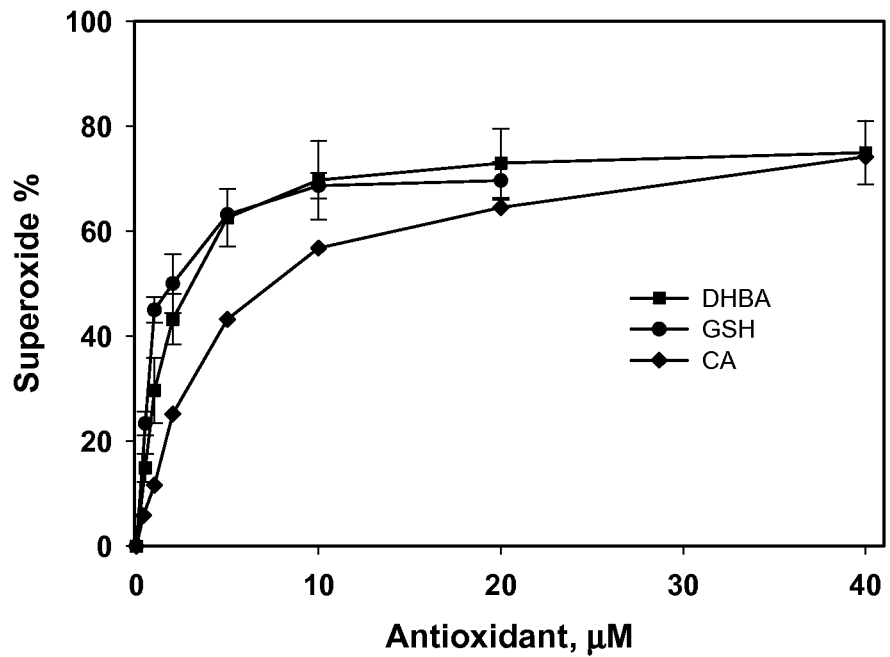
FIG. 11 is a graph showing the concentration dependent superoxide ion scavenging activity of caffeic acid and DHBA. Glutathione (GSH) was used as a control.

DHBA and THB-CHO, at the concentration of 20 μM, had strong scavenging effects on superoxide (FIG. 7D). DHBA had an even stronger superoxide scavenging effect than that of glutathione. The concentration dependent effect of DHBA and caffeic acid on superoxide scavenging was also studied and compared with that of glutathione (FIG. 11).

Figure 7:
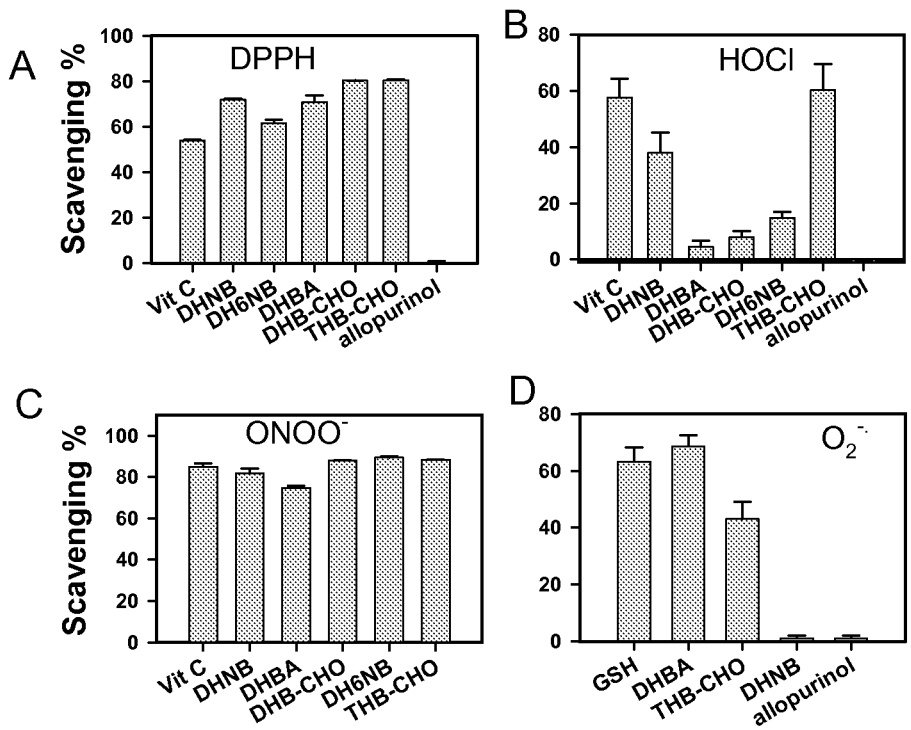
FIG. 7 contains graphs showing the antioxidant activities of DHNB, DH6NB, DHBA, DHB-CHO, THB-CHO, and allopurinol on the scavenging of free radical DPPH (panel A), hypochlorous acid (HOCl) (panel B), peroxynitrite (ONOO$^-$) (panel C), and/or superoxide ion ($O_2^-$·) (panel D). Vitamin C (Vit C) or glutathione (GSH) was used as a control. Each compound was used at a concentration of 20 μM.
Figure 8:
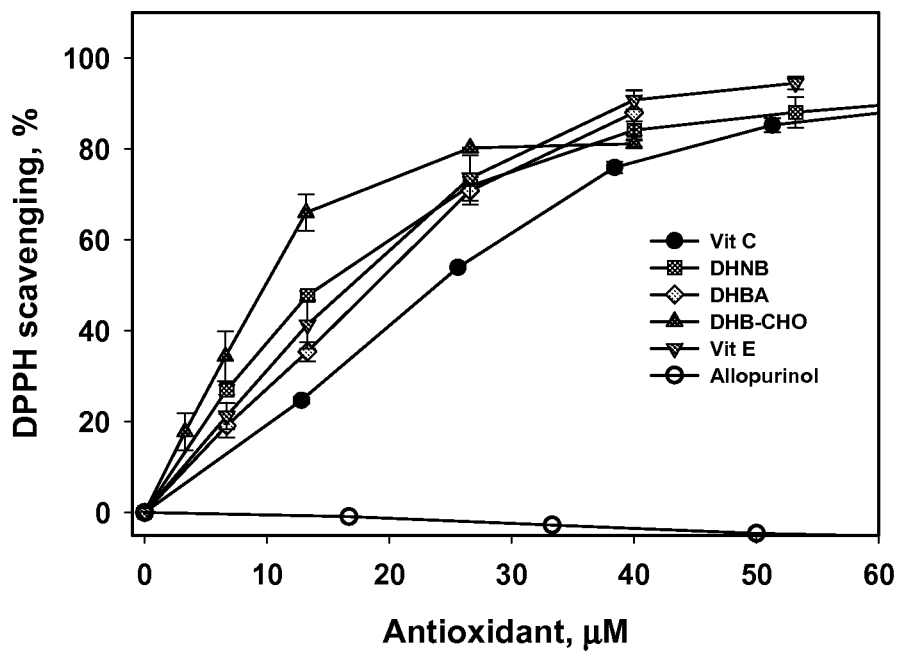
FIG. 8 is a graph showing the concentration dependent DPPH scavenging activities of DHNB, DHBA, DHB-CHO, and allopurinol. Vitamin C (Vit C) and Vitamin E (Vit E) were used as controls.

Antioxidant activity of Polyphenols—Several of the compounds described herein strongly scavenged DPPH, ONOO$^-$, HOCl, and superoxide ion with low IC$_{50}$ values (see FIG. 7). Allopurinol does not possess the antioxidant properties similar to the compounds described herein. Thus, the antioxidant properties of the compounds described herein are an advantage as XO inhibitors over allopurinol.

Example 4

Hypouricemic Effect of DHNB in Allantoxanamide Induced Hyperuricemic Mice

A hyperuricemia mouse model was used. Allantoxanamide, a potent uricase inhibitor, was used to induce hyperuricemia in mice in this study. Briefly, adult C57BL/6 mice (15-25 g, 6-8 weeks old, 6 per group) were administrated DHNB at a concentration of 100 mg/kg in 1.0% polyethylene glycol 400 (PEG400 in a volume of 0.1 ml/10 g mouse body weight) via oral gavage. The mice were subsequently intraperitoneally injected with allantoxanamide at 200 mg/kg in 0.5% CMC-Na in a volume of 0.1 ml/10 g mouse body weight just after the tested drug oral administration to increase the serum uric acid level. Positive control mice were administered allopurinol at the same concentration as DHNB followed by i.p. allantoxanamide. The negative control mice were administered PEG400 only followed by i.p. allantoxanamide. The normal group mice were administered PEG400 only followed by i.p. CMC-Na only. Food and water were withheld overnight prior to the study. Whole blood samples were collected from mice through orbital vein bleeding at the end of the study. The mice were anaesthetized with diethyl ether inside a chamber. The blood was allowed to clot for 1 h at room temperature and then centrifuged at 2350×g for 4 min to obtain the serum. The serum was kept on ice and assayed immediately. Serum uric acid was determined with the phosphotungstate method, as known to those of skill in the art.

Figure 12:
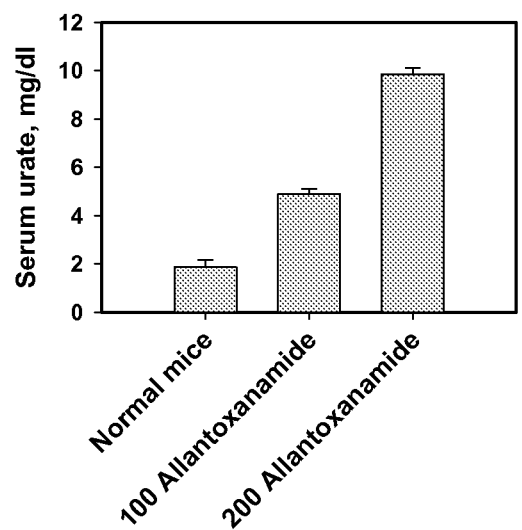
FIG. 12 is a graph showing the dose dependent hyperuricemic effects of allantoxanamide in mice.
Figure 13:
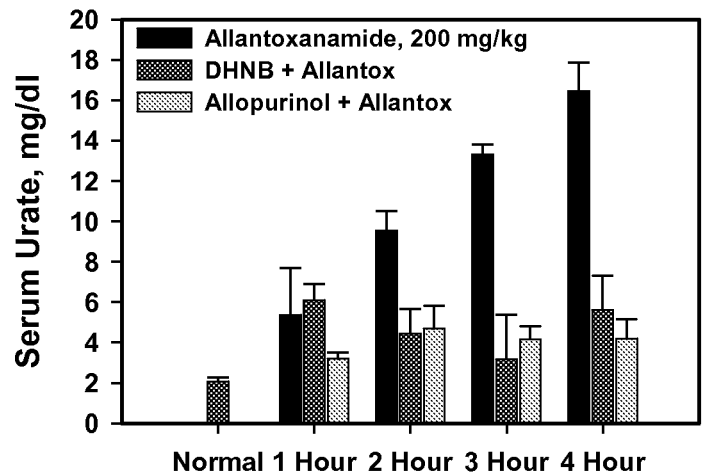
FIG. 13 is a graph showing the time course of the hypouricemic effect of DHNB and allopurinol on the allantoxanamide induced hyperuricemic mice.

Both allantoxanamide and potassium oxonate have been used as uricase inhibitors; however, the hyperuricemic effects of allantoxanamide are stronger and last longer than that of oxonate in rats. A single intraperitoneal injection of 200 mg/kg allantoxanamide in mice progressively increased the serum acid level during the experiment for 4 hours. The serum urate levels were elevated from 2 mg/dl (normal mice) to 5.4, 9.5, 13.3, and 16.4 mg/dl in 1, 2, 3, and 4 h after the allantoxanamide i.p. injection, respectively. In contrast, when the mice were orally administered 100 mg/kg DHNB before the allantoxanamide injection, the serum urate levels were significantly lowered in 2 hours and maintained at a level just slightly higher than the normal level in 4 hours. In comparison, when allopurinol was used in the same condition as that of DHNB, allopurinol also significantly lowered the serum urate level close to the normal level in mice. See FIG. 12 and FIG. 13.

Example 5

Acute Toxicity Studies of DHNB in Mice

To determine whether DHNB has any acute toxicity in mice, C57BL/6 mice were randomized into 3 groups (12/group). Groups 1 to 3 received an oral vehicle solution (PEG400), DHNB (500 mg/kg), and allopurinol (500 mg/kg), respectively. Each mouse was monitored for general health conditions on a daily basis for 28 days, including examination of mortality, body weights, and behavior of the mice.

Figure 14A:
FIG. 14A is a photograph of allopurinol treated mice at 2.5 weeks.
Figure 14B:
FIG. 14B is a photograph of allopurinol treated mice at 3 weeks.
Figure 14C:
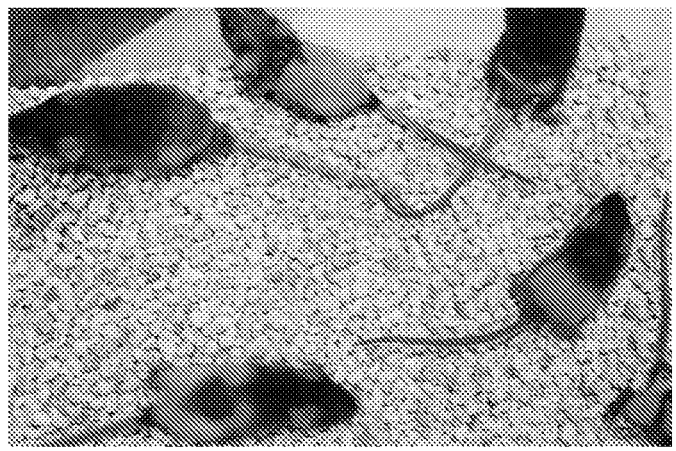
FIG. 14C is a photograph of allopurinol treated mice at 4 weeks.
Figure 14D:
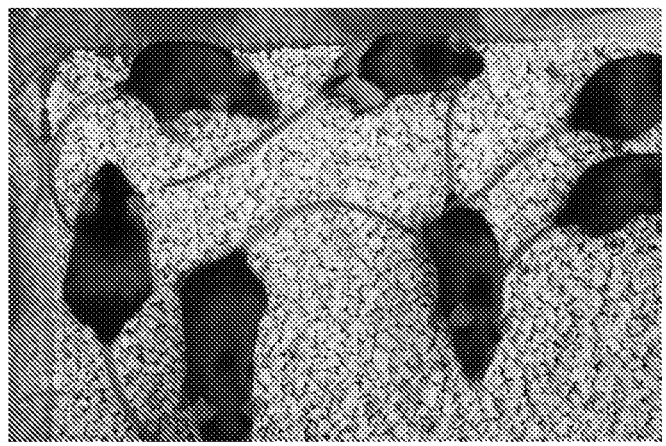
FIG. 14D is a photograph of allopurinol treated mice at 6 weeks.
Figure 14E:
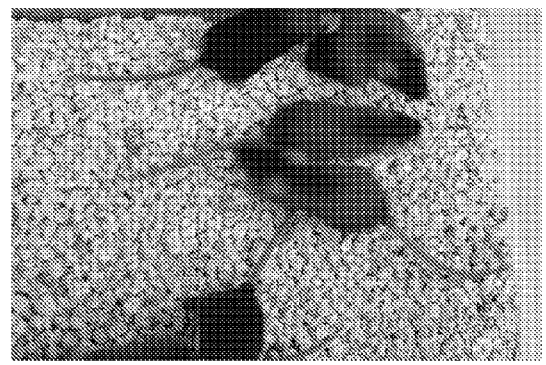
FIG. 14E is a photograph of DHNB treated mice at 4 weeks.

Toxic effects of DHNB are not reported, but the lowest published lethal dose of DHNB in the mouse is 312 mg/kg (oral administration once). DHNB or allopurinol at 500 mg/kg was administrated to 12 mice, respectively, via oral gavage. Control mice received the vehicle solution. The animals were observed daily up to 28 days. DHNB-treated mice did not show any symptoms of general toxicity. There was no difference in body weight and behavior between DHNB-treated mice and control mice. Histology analysis for the liver, kidney, and heart did not show any difference between DHNB-treated mice and control mice. In the allopurinol treated mice, however, 5 mice died within 3 days (mortality 42%). Furthermore, the surviving mice (mixed male and female) gave birth to total 19 pups, but eight died in two days. The survived pups of allopurinol treated mice started to lose hair after two weeks (FIG. 14A) and lost most of the back hair at 3 weeks (FIG. 14B) to 4 weeks (FIG. 14C). After separated from the adult mice, the pups started to grow hair again and returned to normal hair at the age of 6 to 7 weeks (FIG. 14D). However, this hair loss phenomenon was not observed on DHNB treated mice (see FIG. 14E for DHNB treated mice at 4 weeks). A summary of the in vivo toxicities of DHNB and allopurinol in mice is shown in Table 1.

TABLE 1

| 12 Mice/group | | Behavior | Organs | Mortality | 2$^{nd}$ Generation Mortality | Hair Loss |
|---|---|---|---|---|---|---|
| DHNB | 100 | Normal | Normal | None | N/A | None |
| mg/kg | 200 | Normal | Normal | None | N/A | None |
| | 500 | Normal | Normal | None | None | None |
| Allopurinol 500 mg/kg | | Normal for survivors | N/A | Average 42% | Average 42% | 1$^{st}$ batch, 100% 2$^{nd}$ batch, 50% 3$^{rd}$ batch, 20% |

Example 6

XO Inhibition Assay

XO inhibition assays were performed on the compounds shown below in Scheme 2 using the methods as described in Example 1.

Scheme 2:

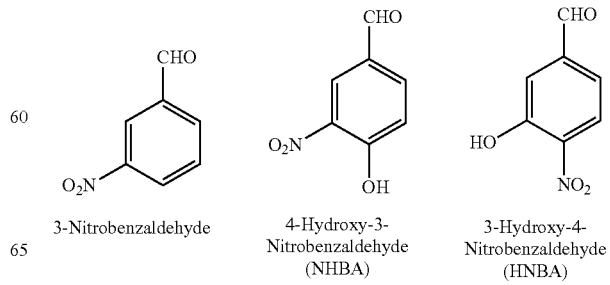

3-Nitrobenzaldehyde    4-Hydroxy-3-Nitrobenzaldehyde (NHBA)    3-Hydroxy-4-Nitrobenzaldehyde (HNBA)

-continued

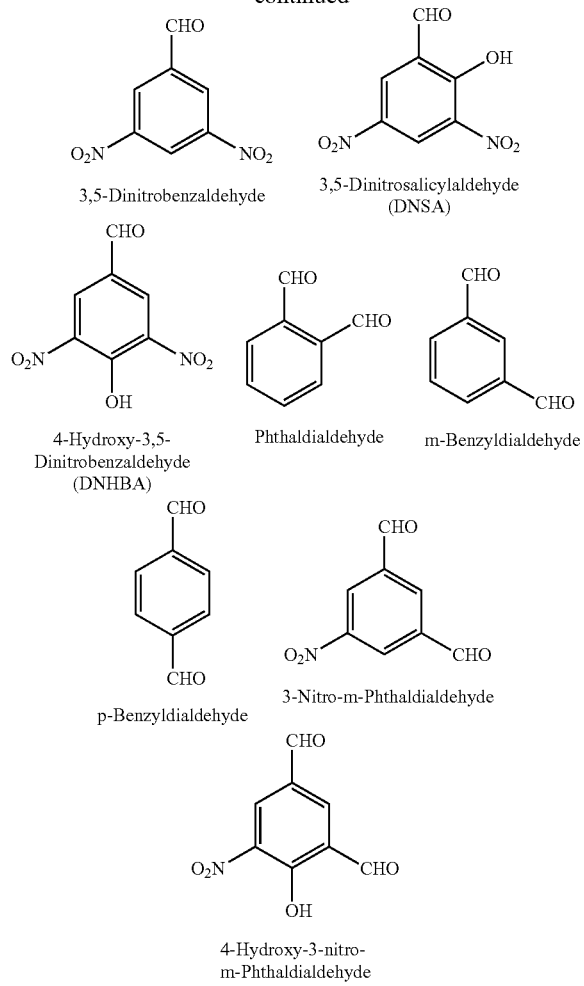

Figure 15A:
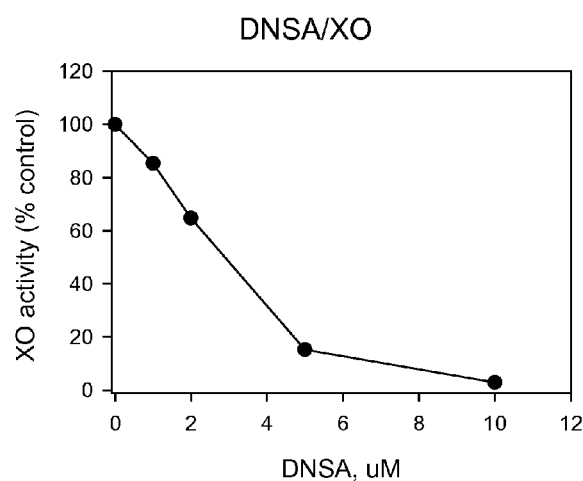
FIGS. 15A and 15B are graphs showing the inhibitory effects of DNSA and NHBA, respectively, on XO activity by measuring the initial rate of uric acid formation.
Figure 15B:
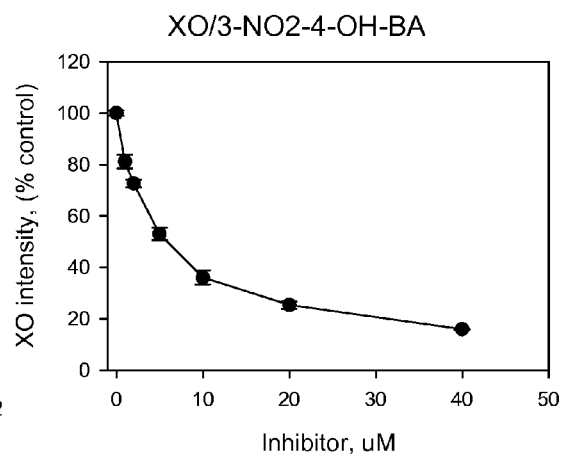

The inhibitory effects of DNSA and NHBA on XO activity were determined by measuring the initial rate of formation of uric acid. Following exposure of XO (5 milliunits/ml) to a 0-10 µM concentration of DNSA or a 0-40 µM concentration of NHBA in 33 mM phosphate buffer (pH 7.4, 25° C.), XO activity was determined by the production of uric acid (295 nm). Reactions were initiated by the addition of xanthine (50 µM). The results are shown in FIGS. 15A and 15B.

Figure 16:
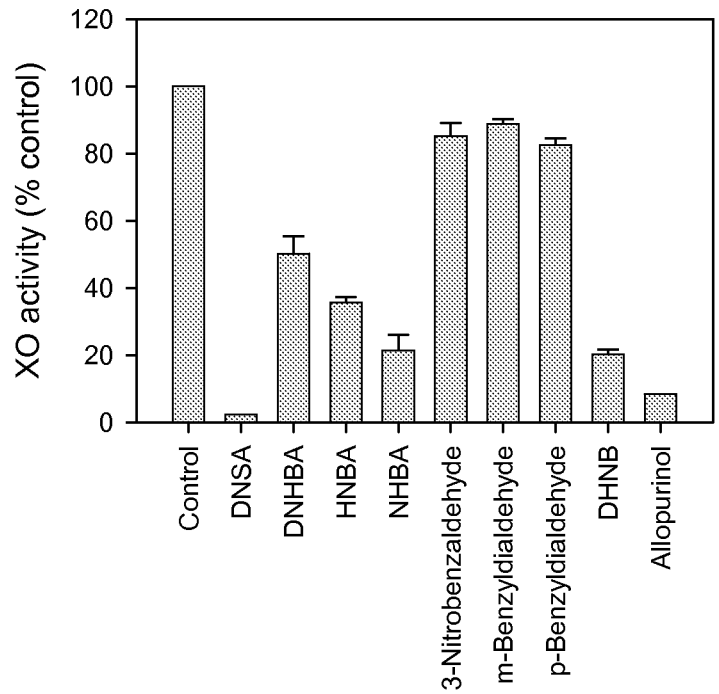
FIG. 16 is a graph comparing the xanthine oxidase inhibitory effects of catechol compounds at a concentration of 20 μM. The control represents no inhibitor added.

The XO inhibition effects of the compounds shown in Scheme 2 were compared at a concentration of 20 µM. XO activity was determined by measuring the initial rate of formation of uric acid (λ=295 nm) as in FIGS. 15A-B. After pre-incubation of 20 nM XO and 20 µM inhibitor for 10 min, 50 µM xanthine was added to initiate the reaction. Data represent the mean±S.E. of at least three independent determinations and are shown in FIG. 16.

Figure 17:
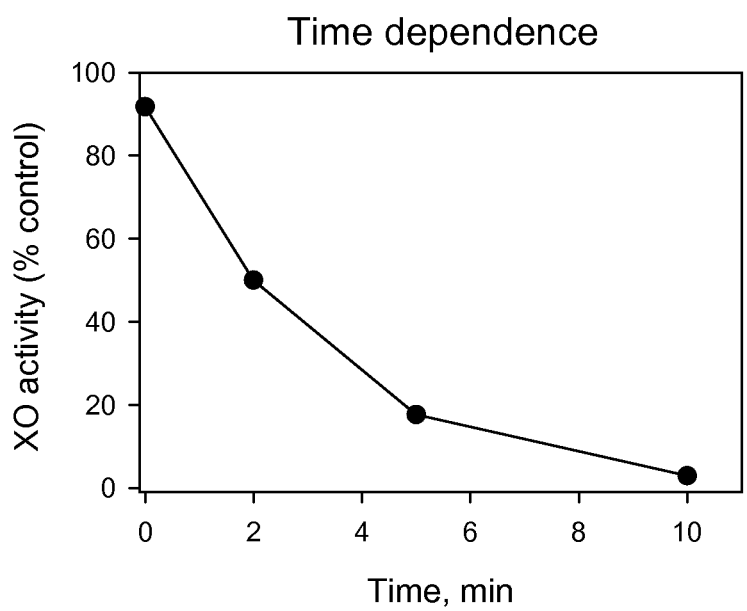
FIG. 17 is a graph demonstrating the influence of pre-incubation of DNSA with XO on XO activity.

The influence of pre-incubation of DNSA with XO on the XO activity was determined. XO activity was determined by the steady-state rate of formation of uric acid (λ=295 nm) by pre-incubation of 20 nM XO and 20 µM DNSA for 0-10 min followed by the addition of 50 µM xanthine to start the reaction. Data represent one of three independent determinations for DNSA. Pre-incubation of DNSA with XO strongly inhibited XO activity. The results are shown in FIG. 17.

Figure 18:
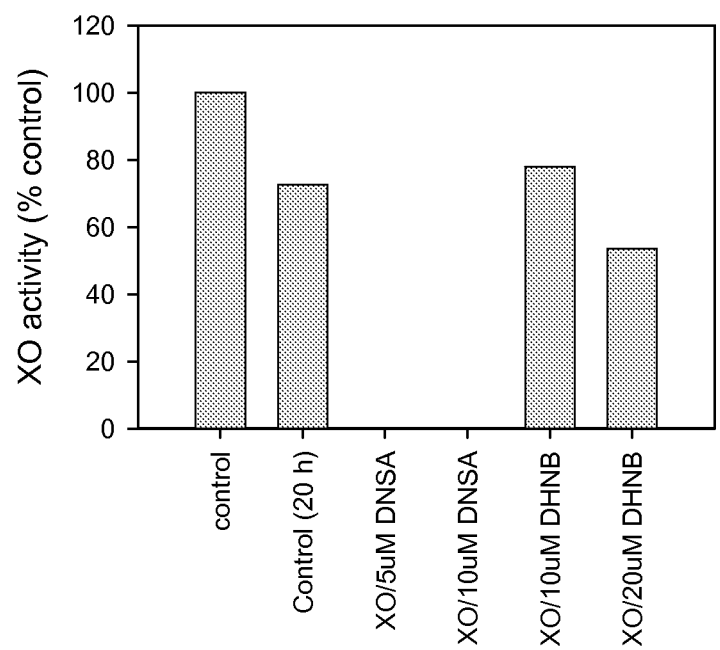
FIG. 18 is a graph demonstrating XO activity after pre-incubation with inhibitors DNSA and DHNB for 20 hours.

The XO activities after pre-incubation with DNSA and DHNB for 20 h were determined. XO stored at room temperature for 20 h decayed in 30% activity, but XO/DNSA (5 µM or 10 µM) samples showed no XO activity at all and DNSA was not converted. For XO/DHNB samples, XO activity was recovered, and DHNB was converted to DHNB-COOH completely. The results are shown in FIG. 18.

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods and combinations of various features of the compounds and methods are intended to fall within the scope of the appended claims, even if not specifically recited. Thus, a combination of steps, elements, components, or constituents may be explicitly mentioned herein; however, all other combinations of steps, elements, components, and constituents are included, even though not explicitly stated.

What is claimed is:

1. A method for treating gout or hyperuricemia in a subject comprising administering to the subject an effective amount of a compound selected from the group consisting of:

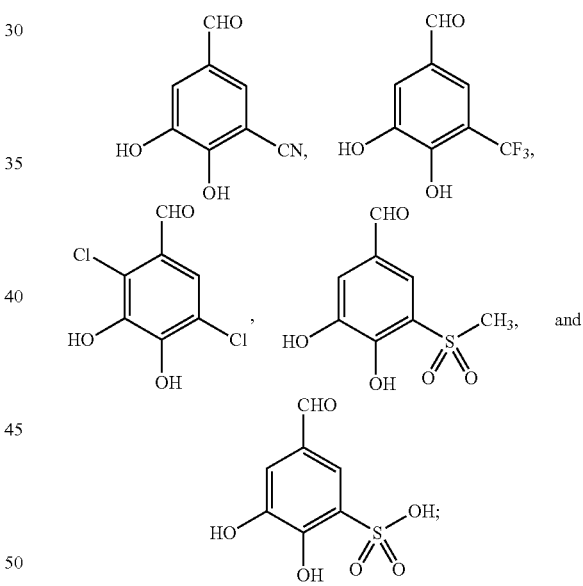

or a pharmaceutically acceptable salt thereof.

2. The method of claim 1, further comprising administering a second therapeutic agent to the subject.

3. The method of claim 1, wherein the second therapeutic agent is an anti-gout agent.

4. The method of claim 3, wherein the anti-gout agent is selected from the group consisting of allopurinol, benzbromarone, colchicine, probenecid, and sulfinpyrazone.

5. The method of claim 1, wherein the second therapeutic agent is an anti-inflammatory agent.

6. The method of claim 1, wherein the second therapeutic agent is an antioxidant.

7. The method of claim 1, wherein the compound is administered orally.

* * * * *